United States Patent
Cronstein et al.

(10) Patent No.: US 7,795,427 B2
(45) Date of Patent: Sep. 14, 2010

(54) METHODS FOR INHIBITING OSTEOCLAST DIFFERENTIATION, FORMATION, OR FUNCTION AND FOR INCREASING BONE MASS

(75) Inventors: Bruce N. Cronstein, New York, NY (US); Firas Mohamed Kara, Woodside, NY (US)

(73) Assignee: New York University, New York, NY (US)

( * ) Notice: Subject to any disclaimer, the term of this patent is extended or adjusted under 35 U.S.C. 154(b) by 401 days.

(21) Appl. No.: 11/705,689

(22) Filed: Feb. 13, 2007

(65) Prior Publication Data

US 2007/0191279 A1 Aug. 16, 2007

Related U.S. Application Data

(60) Provisional application No. 60/773,176, filed on Feb. 14, 2006.

(51) Int. Cl.
 *C07D 473/00* (2006.01)
(52) U.S. Cl. ........................................ 544/267; 424/9.2
(58) Field of Classification Search ........................ None
 See application file for complete search history.

(56) References Cited

U.S. PATENT DOCUMENTS

| | | | |
|---|---|---|---|
| 4,069,321 A * | 1/1978 | Jones et al. | 514/167 |
| 5,462,932 A * | 10/1995 | Brenner et al. | 514/108 |
| 5,786,360 A | 7/1998 | Neely | |
| 5,840,729 A | 11/1998 | Hitchcock et al. | |
| 5,843,678 A | 12/1998 | Boyle | |
| 6,017,729 A | 1/2000 | Anderson et al. | |
| 6,117,998 A | 9/2000 | Neely | |
| 6,489,332 B1 | 12/2002 | Neely | |
| 6,495,687 B1 | 12/2002 | Neely | |
| 6,605,601 B2 | 8/2003 | Lin et al. | |
| 6,627,632 B2 * | 9/2003 | Parks et al. | 514/252.19 |
| 6,806,270 B2 * | 10/2004 | Biaggioni et al. | 514/234.2 |
| 6,916,790 B2 * | 7/2005 | Khosla et al. | 514/21 |
| 7,358,374 B2 * | 4/2008 | McLaughlin et al. | 548/570 |
| 7,465,703 B1 * | 12/2008 | Cantor | 514/2 |
| 7,553,484 B2 * | 6/2009 | Kaufman et al. | 424/130.1 |
| 2002/0082269 A1 | 6/2002 | Neely | |
| 2002/0103161 A1 | 8/2002 | Weigele et al. | |
| 2002/0111333 A1 | 8/2002 | Lin et al. | |
| 2003/0045536 A1 | 3/2003 | Castelhano et al. | |
| 2003/0220358 A1 | 11/2003 | Lin et al. | |
| 2005/0059683 A1 | 3/2005 | Zablocki et al. | |
| 2005/0119258 A1 | 6/2005 | Wilson et al. | |
| 2005/0187226 A1 | 8/2005 | Wilson et al. | |
| 2005/0245546 A1 | 11/2005 | Cristalli | |

OTHER PUBLICATIONS

Gimenez-Llort, L. et al. (2002) Eur J. Neurosci 16:547-550.
Johansson, B. et al (2001) Proc Natl Acad Sci U.S.A. 98:9407-9412.

* cited by examiner

*Primary Examiner*—Lorraine Spector

(57) ABSTRACT

The invention provides methods and compositions for modulating osteoclastogenesis and for treating bone diseases characterized by bone loss or a decrease in bone mass or density, by administering a compound or agent that modulates the adenosine A1 receptor, in particular, an inhibitor or antagonist of the A1 receptor.

29 Claims, 12 Drawing Sheets

TRAP+ Osteoclasts Do not Associate with Bone in A₁ Knockout Mice

Wild Type

A₁ Knockout

METHODS FOR INHIBITING OSTEOCLAST DIFFERENTIATION, FORMATION, OR FUNCTION AND FOR INCREASING BONE MASS

CROSS-REFERENCE TO RELATED APPLICATIONS

The present application is a non-provisional application claiming the priority of copending provisional application Ser. No. 60/773,176, filed Feb. 14, 2006, the disclosure of which is incorporated by reference herein in its entirety. Applicants claim the benefits of this application under 35 U.S.C. §119 (e).

FIELD OF THE INVENTION

The present invention relates to methods and compositions for modulating the processes of bone formation and/or bone loss, thereby providing novel treatments for bone diseases. The present invention also relates to methods for screening osteogenic compounds, including compounds which modulate osteoclast differentiation, formation and function. The present invention further encompasses compounds identified by such screening methods and compositions comprising these compounds. More particularly, the present invention relates to methods and compositions comprising adenosine A1 receptor antagonists that act to inhibit osteoclast differentiation, osteoclast formation or osteoclast function. Such adenosine A1 receptor antagonists may be used to treat subjects suffering from, or at risk for developing, diseases or conditions characterized by bone loss or low bone mass.

BACKGROUND OF THE INVENTION

Various conditions and diseases which manifest themselves in bone loss or thinning are a critical and growing health concern. It has been estimated that as many as 30 million Americans and 100 million worldwide are at risk for osteoporosis alone (Mundy et al. (1999) Science 286:1946-1949). Other conditions known to involve bone loss include juvenile osteoporosis, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, bone fractures, periodontal bone loss, age-related loss of bone mass, osteotomy and bone loss associated with prosthetic ingrowth and other forms of osteopenia. Additionally, new bone formation is needed in many situations, e.g., to facilitate bone repair or replacement for bone fractures, bone defects, plastic surgery, dental and other implantations and in other such contexts.

Bone is a dense, specialized form of connective tissue. Bone matrix is formed by osteoblast cells located at or near the surface of existing bone matrix. Bone is resorbed (eroded) by another macrophage-type cell type known as the osteoclast. Osteoclasts secrete acids, which dissolve bone minerals, and enzymes, particularly hydrolases, which digest its organic components. Osteoclasts originate from hematopoietic precursors of the monocyte/macrophage lineage and migrate to the bone environment. Here, in the presence of the cytokines RANKL (receptor activator of NF-κB ligand) and M-CSF (macrophage colony stimulating factor), they fuse to form multinuclear cells and assume the unique osteoclast phenotype and acquire the capacity to degrade mineralized matrix [Boyle W J, Simonet W S, Lacey D L. (2003), Osteoclasts differentiation and activation. Nature 15:337-342; Teitelbaum S L. (2000), Bone resorption by osteoclasts. Science 289:1504-1508]. Osteoclasts, which are the sole bone resorbing cells, are essential for skeletal development and remodeling throughout the life of animal and man. A deficiency of osteoclasts leads to osteopetrosis, a disease manifested by increased non-remodeled bone mass, which ultimately leads to bone deformities and functional failure of other body systems. On the other hand, an increase in the number and activity of osteoclasts causes accelerated bone resorption and may lead to osteoporosis and osteolytic diseases. Thus, proper bone formation and remodeling is a dynamic process that involves an ongoing interplay between the creation and erosion activities of osteoblasts and osteoclasts (Alberts, et al., Molecular Biology of the Cell, Garland Publishing, N.Y. (3rd ed. 1994), pp. 1182-1186).

Most bone diseases are due to increased bone resorption, rendering its inhibition a primary therapeutic objective. Indeed, most osteoporosis therapies that are currently available belong in this category. Inhibition of bone resorption can be accomplished by reducing osteoclast formation and activity. These processes point to rate-limiting steps in osteoclast formation and function, and offer a number of targets for therapeutic intervention.

It has recently become clear that such molecules as receptor activator of NF-κB (RANK), RANK ligand (RANKL), and osteoprotegerin, a soluble protein that binds to RANKL and prevents its ligation to its receptor are involved in the regulation of osteoclastogenesis. RANKL stimulates osteoclastogenesis through binding to its receptor RANK on osteoclast precursors. The isolation, cloning and production of RANKL further permitted the study of osteoclastogenesis under in vitro conditions. More particularly, RANK ligand (RANKL, also known as osteoprotegerin ligand (OPGL), TNF-related activation induced cytokine (TRANCE), and osteoclast differentiation factor (ODF)), expressed on stromal cells, osteoblasts, activated T-lymphocytes and mammary epithelium, is the unique molecule essential for differentiation of macrophages into osteoclasts (Lacey, et al. (1998) Cell 93: 165-176). The cell surface receptor for RANKL is RANK, Receptor Activator of Necrosis Factor (NF)-kappa B. RANKL is a type-2 transmembrane protein with an intracellular domain of less than about 50 amino acids, a transmembrane domain of about 21 amino acids, and an extracellular domain of about 240 to 250 amino acids. RANKL exists naturally in transmembrane and soluble forms. The deduced amino acid sequence for at least the murine, rat and human forms of RANKL and variants thereof are known. (See e.g., Anderson, et al., U.S. Pat. No. 6,017,729, Boyle, U.S. Pat. No. 5,843,678, and Xu J. et al., J. Bone Min. Res. (2000) 15:2178) which are incorporated herein by reference in their entirety. RANKL (OPGL) has been identified as a potent inducer of bone resorption and as a positive regulator of osteoclast development. (Lacey et al., supra.).

RANK signaling, activated by its ligand RANKL, which is expressed on stromal cells and osteoblasts [Suda T, Takahashi N, Udagawa N, Jimi E, Gillespie M T, Martin T J. (1999), Modulation of osteoclast differentiation and function by the new members of the tumor necrosis factor receptor and ligand families. Endocr Rev 20:345-357], is mediated by a series of protein kinases including c-Src, c-Jun N terminal kinase (JNK), p 38, extracellular signal related kinase (ERK), phosphoinositol-3-kinase (PI-3K), and those activating NF-κB [Darnay B G, Haridas V, Ni J, Moore P A, Aggarwal B B, (1998), Characterization of the intracellular domain of receptor activator of NF-kappaB (RANK). Interaction with tumor necrosis factor receptor-associated factors and activation of NF-kappaβ and c-Jun N-terminal kinase. J Biol Chem 273: 20551-2055; Galibert L, Tometsko M E, Anderson D M, Cosman D, Dougall, W C. (1998), The involvement of multiple tumor necrosis factor receptor (TNFR)-associated factors in the signaling mechanisms of receptor activator of NF-kappaB, a member of the TNFR superfamily. J Biol Chem 273:34120-34127; Lee S E, Woo K M, Kim S Y, Kim H-M, Kwack K, Lee Z H, Kim H-H. (2002), The phosphatidylinositol 3-Kinase, p 38, and extracellular signal-regulated kinase pathways are involved in osteoclast differentiation. Bone 30:71-77; Matsumoto M, Sudo T, Saito T, Osada A, Tsujimoto M. (2000), Involvement of p38 mitogen-activated protein kinase signaling pathway in osteoclastogenesis mediated by receptor activator of NF-kappa B ligand (RANKL). J Biol Chem 275:31155-31161]. M-CSF, which via, its receptor, c-Fms, stimulates many of the same pathways, promotes proliferation of osteoclast precursors and survival of the mature resorptive cell [Tanaka S, Takahashi N, Udagawa N, Tamura T, Akatsu T, Stanley E R, Kurokawa T, Suda T. (1993), Macrophage colony-stimulating factor is indispensable for both proliferation and differentiation of osteoclast progenitors. J Clin Invest 91:257-263; Woo K M, Kim H M, Ko J S. (2002), Macrophage colony-stimulating factor promotes the survival of osteoclast precursors by up-regulating Bcl-XL. Exp Mol Med 34:340-346]. Together, therefore, RANKL and M-CSF induce expression of genes, such as those encoding tartrate-resistant acid phosphatase (TRAP), cathepsin K (CATK), calcitonin receptor and β3 integrin, which characterize the mature osteoclast and its committed precursors [Faccio R, Zallone A, Ross F P, Teitelbaum S L. (2003), c-Fms and the avb3 integrin collaborate during osteoclast differentiation. J Clin Invest 111:749-758; Kudo O, Sabokbar A, Pocock A, Itonaga I, Athanasou N A. (2002). Isolation of human osteoclasts formed in vitro: hormonal effects on the bone-resorbing activity of human osteoclasts. Calcif Tissue Int 71:539-546]

The fact that osteoclasts are derived from macrophages, which are professional phagocytes of myeloid origin that reside in all tissues and organs and are cells that are fundamental to immune recognition, has led to a series of experiments which link the immune system to osteoclast recruitment and function. For example, T-lymphocyte-produced cytokines, including RANKL and TNFα, appear central to the enhanced osteoclastogenesis responsible for the bone loss attending menopause and the peri-articular bone erosions of rheumatoid arthritis [Cenci S, Weitzmann M N, Roggia C, Namba N, Novack D, Pacifici R. (2000), Estrogen deficiency induces bone loss by enhancing T cell production of TNFα. J Clin Invest 106:1229-1237; Romas E, Gillespie M T, Martin T J. (2002), Involvement of receptor activator of NFκB ligand and tumor necrosis factor-alpha in bone destruction in rheumatoid arthritis. Bone 30:340-346; Weitzmann M N, Cenci S, Rifas L, Brown. C., Pacifici R. (2000), IL-7 stimulates osteoclast formation by upregulating the T-cell production of soluble osteoclastogenic cytokines. Blood 96:1873-1878]. In this context, the process of antigen presentation, itself, is also a fundamental event in pathological osteoclastogenesis [Jenkins J K, Hardy K J, McMurray RW. (2002), The pathogenesis of rheumatoid arthritis: a guide to therapy. Am J Med Sci 323:171-180]. Under appropriate conditions, macrophages may fuse with each other to form multinucleate giant cells which are descriptively separated into foreign body and Langerhans giant cells by the organization of the nuclei within the cell. In bone, macrophages fuse to form osteoclasts which mediate bone resorption (Johansson, B., Halldner, L., Dunwiddie, T. V., Masino, S. A., Poelchen, W., Gimenez-Llort, L., Escorihuela, R. M., Femandez-Teruel, A., Wiesenfeld-Hallin, Z., Xu, X. J., et al. (2001), Hyperalgesia, anxiety, and decreased hypoxic neuroprotection in mice lacking the adenosine A1 receptor. *Proc Natl Acad Sci USA* 98:9407-9412) both in normal day-to-day bone remodeling and in such pathologic situations as osteoporosis, inflammatory arthritis with bony erosions, peri-prosthetic bone resorption, hypercalcemia of malignancy and bone metastases (Gimenez-Llort, L., Fernandez-Teruel, A., Escorihuela, R. M., Fredholm, B. B., Tobena, A., Pekny, M., and Johansson, B. (2002), Mice lacking the adenosine A1 receptor are anxious and aggressive, but are normal learners with reduced muscle strength and survival rate. *Eur J Neurosci* 16:547-550). Fusion of macrophages is critical for the differentiation of osteoclasts, as mononuclear macrophages cannot resorb bone efficiently.

The major characteristics of osteoclasts which differentiate them from other forms of giant cells include: tartrate-resistant acid phosphatase (TRAP) staining (shared with macrophages), multinuclearity, formation of actin ring structure and a polar cell body during resorption, and contraction in response to calcitonin, expression of molecular markers including the calcitonin receptor, RANK (receptor of RANKL), receptor activator of NFκB ligand), c-fms (receptor of M-CSF, macrophage-colony stimulating factor), cathepsin K, c-src, fosL1 and the vitronectin receptor (integrin αvβ3).

Adenosine is a nucleoside that occurs naturally in mammals, which acts as a ubiquitous biochemical messenger. The heart, for instance, produces and releases adenosine in order to modulate heart rate and coronary vasodilation. Likewise, adenosine is produced in the kidney to modulate essential physiological responses, including glomerular filtration rate (GFR), electrolyte reabsorption, and renin secretion.

Adenosine is known to bind to and activate seven-transmembrane spanning G-protein coupled receptors, thereby eliciting a variety of physiological responses. There are 4 known subtypes of adenosine receptors (i.e., A1, A2a, A2b, and A3), which mediate different, and sometimes opposing, effects. For example, activation of the adenosine A1 receptor, elicits an increase in renal vascular resistance, which leads to a decrease in glomerular filtration rate (GFR), while activation of the adenosine A2a receptor elicits a decrease in renal vascular resistance. Conversely, blockade of the A1 adenosine receptor decreases afferent arteriole pressure, leading to an increase in GFR and urine flow, and sodium excretion. Furthermore, A2A adenosine receptors modulate coronary vasodilation, whereas A2B receptors have been implicated in mast cell activation, asthma, vasodilation, regulation of cell growth, intestinal function, and modulation of neurosecretion (See Adenosine A2B Receptors as Therapeutic Targets, Drug Dev Res 45:198; Feoktistov et al., Trends Pharmacol Sci 19:148-153 and Ralevic, V and Burnstock, G. (1998), Pharmacological Reviews, Vol. 50: 413-492), and $A_3$ adenosine receptors modulate cell proliferation processes. Two receptor subtypes (A1 and A2a) exhibit affinity for adenosine in the nanomolar range while two other known subtypes A2b and A3 are low-affinity receptors, with affinity for adenosine in the low-micromolar range. A1 and A3 adenosine receptor activation can lead to an inhibition of adenylate cyclase activity, while A2a and A2b activation causes a stimulation of adenylate cyclase.

Diseases that can be prevented and/or treated with A1 adenosine receptor antagonists include diseases and disorders wherein activation of A1 adenosine receptors plays a role in pathophysiology. For example, A1 adenosine receptor antagonists are useful for treating cognitive disorders and dementias such as Alzheimers disease, and for treating stress, depression, cardiac arrhythmia, restoration of cardiac function, congestive heart failure, asthma, and respiratory disorders (e.g., bronchial asthma, allergic lung diseases). They also reduce ischemia-induced injury of the brain, heart and kidney. A1 adenosine receptor antagonists have pronounced effects on the kidney, and have shown to be potent diuretics and natriuretics with little effective on potassium excretion. Thus, they are also renal protective, useful for the treatment of renal failure, renal dysfunction, nephritis, hypertension, and edema. It has been suggested that A2a antagonists may be beneficial for patients suffering from Morbus Parkinson (Parkinson's disease). Adenosine receptor antagonists may also be valuable for treatment of allergic inflammation and asthma. Available information (for example, Nyce & Metzger "DNA antisense Therapy for Asthma in an Animal Model" Nature (1997) 385: 721-5) indicates that in this pathophysiologic context, A1 antagonists may block contraction of smooth muscle underlying respiratory epithelia, while A2b or A3 receptor antagonists may block mast cell degranulation, mitigating the release of histamine and other inflammatory mediators. A2b receptors have been discovered throughout the gastrointestinal tract, especially in the colon and the intestinal epithelia. It has been suggested that A2b receptors mediate cAMP response (Strohmeier et al., J. Bio. Chem. (1995) 270:2387-94).

There is a need for new agents that are effective for treating subjects suffering from conditions characterized by loss of bone, or for treating subjects at risk for developing such conditions. There is also a need for more effective treatment strategies for increasing bone mass in subjects suffering from diseases, disorders, or conditions that lead to decreased bone density. These needs are addressed by the agents and methods of the present invention.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention.

SUMMARY OF THE INVENTION

The invention relates to the application and use of modulators of an adenosine receptor, including inhibitors or antagonists of an adenosine receptor, to inhibit osteoclast differentiation, formation or function. More particularly, the invention provides for the use of an A1 receptor antagonist for treating, ameliorating, or preventing bone diseases or conditions that are characterized by, or result in, low bone mass. The invention relates to the use of such inhibitors or antagonists of the adenosine A1 receptor for treating, ameliorating or preventing a bone disease or a condition in a subject having such disease or condition, or in a subject at risk for developing such disease or condition, particularly wherein it is desired to reduce or control osteoclast function or differentiation, including but not limited to osteoporosis, juvenile osteoporosis, bone loss due to/or associated with the onset of menopause, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, periodontal bone loss, age-related loss of bone mass, osteotomy and bone loss associated with prosthetic ingrowth, other forms of osteopenia, and in other conditions where facilitation of bone repair or replacement is desired such as bone fractures, bone defects, plastic surgery, dental and other implantations.

Accordingly, a first aspect of the invention provides a method for inhibiting osteoclast differentiation, formation, or function, comprising administering an agent that blocks or antagonizes an adenosine receptor, in an amount sufficient to inhibit osteoclast differentiation, formation or function.

A second aspect of the invention provides a method for treating a subject having a condition characterized by low bone mass, or for preventing the condition in a subject prone to developing the condition, comprising administering to the subject a therapeutically effective amount of an adenosine receptor antagonist, or an analog, derivative or combination thereof.

A third aspect of the invention provides a method of increasing bone mass or ameliorating loss of bone mass in a subject suffering from a condition characterized by low bone mass, the method comprising administering to the subject a therapeutically effective amount of an adenosine receptor antagonist, or an analog, derivative or combination thereof.

In one particular embodiment, the adenosine receptor is selected from the group consisting of A1, A2A, A2B and A3. In a more particular embodiment, the adenosine receptor is an A1 receptor, and the antagonist is an adenosine A1 receptor antagonist. In yet another embodiment, the adenosine receptor antagonist inhibits osteoclastogenesis by acting on osteoclast precursors. In another embodiment, the blocking of adenosine receptors with an antagonist results in loss of TRAF6, a critical intermediate mediator of NF-κB activation, from the cell. In another particular embodiment, the adenosine receptor antagonist acts on distal events in RANK signaling, including, but not limited to, activation of the NF-κB complex via TRAF6. In a more particular embodiment, the adenosine receptor antagonist acts on RANKL-induced degradation of IκB. RANKL induces nuclear translocation of p50 and p65 subunits, decreases the cytoplasmic levels of these two proteins, and also induces degradation of IκB. The addition of an adenosine receptor antagonist prevents the nuclear translocation of p50 and p65 and causes these proteins to accumulate in the cytoplasm and prevent degradation of IκB. Furthermore, in yet another embodiment, the adenosine receptor antagonist prevents bone loss due to ovariectomy, and thus may be effective in the treatment of pathologic bone loss due to menopause, or other diseases or therapies where pathologic bone loss is evident, such as that associated with glucocorticoid treatment.

In another particular embodiment, the condition characterized by low bone mass is selected from the group consisting of osteoporosis, juvenile osteoporosis, bone loss due to/or associated with the onset of menopause, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, periodontal bone loss, age-related loss of bone mass, osteotomy and bone loss associated with prosthetic ingrowth, and other forms of osteopenia. In another particular embodiment, other conditions where facilitation of bone repair or replacement is desired is selected from the group consisting of bone fractures, bone defects, plastic surgery, dental and other implantations.

In another particular embodiment, the adenosine receptor antagonist is a selective or a non-selective adenosine receptor antagonist.

In yet another particular embodiment, the adenosine receptor antagonist is a xanthine derivative or a non-xanthine receptor antagonist.

In a more particular embodiment, the agent that antagonizes an adenosine receptor is an adenosine A1 receptor antagonist. The adenosine A1 receptor antagonist may be a small organic molecule, a protein or peptide, a nucleic acid or an antibody.

In yet another more particular embodiment, the adenosine A1 receptor antagonist is selected from the group consisting of DPCPX (8-Cyclopentyl-1,3-dipropylxanthine), N-0861 (N-6-endonorboman-2-yl-9-methyladenine), N-0840 (N-6-cyclopentyl-9-methyladenine), CVT-124, WRC-0342 ([$N^6$-(5'-endohydroxy)-endonorbornan-2-yl-9-methyladenine]), CGS-15943, XAC (xanthine carboxylic acid congener), WRC-0571 ([$C^8$-(N-methylisopropyl)-amino-$N^6$(5'-endohydroxy)-endonorbornan-2-yl-9-methyladenine],), KW-3902 (8-(noradamantan-3-yl)-1,3-dipropylxanthine), ENX (1,3-Dipropyl-8-[2-(5,6-epoxy)norbornyl]xanthine), KFM 19 (BIIP20, (S)-3,7-dihydro-8-(3-oxocyclopentyl)-1,3-dipropyl-1H-purine-2,6-dione), FK453 ((R)-1-[(E)-3-(2-phenylpyrazolo[1,5-a]pyridin-3-yl) acryloyl]-2-piperidine ethanol), FK352 ((R)-1-[(E)-3-(2-phenylpyrazolo[1,5-a]pyridin-3-yl) acryloyl]-piperidin-2-yl acetic acid), FK838 (6-oxo-3-(2-phenylpyrazolo[1,5-a]pyridin-3-yl)-1(6H)-pyridazinebutyric acid), FR166124 and its analogues, 8-cyclopentyltheophylline, BG9719 and BG9928.

In yet another particular embodiment, the adenosine A1 receptor antagonist is administered orally or parenterally. It may be administered intravenously, subcutaneously, intramuscularly, or intranasally, or it may be administered via an implanted device, or may be administered to a mucous membrane. The implanted device may be an osmotic pump. The mucous membrane may be the oral or nasal mucosa selected from the group consisting of the buccal mucosa, the sublingual mucosa, the sinuidal mucosa, the gum, and the inner lip.

A fourth aspect of the invention provides a method for treating a bone disease or condition in a mammal comprising administering to the mammal an effective amount of an adenosine receptor antagonist in combination with a therapeutically effective amount of one or more other compounds effective for treating a bone disease or condition characterized by loss of bone or a decrease in bone mass.

In one particular embodiment, an effective amount of an adenosine A1 receptor antagonist may be used in combination with one or more antiresorptive drugs, one or more bone-forming agents, one or more estrogen receptor antagonists and one or more drugs that have a stimulatory effect on osteoclasts, or a combination of any of these agents.

In another more particular embodiment, the antiresorptive drug is selected from the group consisting of a bisphosphonate, an estrogen or estrogen analogue, a selective estrogen receptor modulator (SERM) and a calcium source, Tibolone, calcitonin, a calcitriol and hormone replacement therapy.

In yet another more particular embodiment, the bone-forming agent is parathyroid hormone (PTH) or a peptide fragment thereof, PTH-related protein (PTHrp), bone morphogenetic protein, osteogenin, NaF, a $PGE_2$ agonist, a statin, and a RANK ligand (RANKL). In another particular embodiment, the PTH peptide fragment is teriparatide (recombinant human PTH, which consists of the first 34 amino acids of the 84 amino acids of human PTH).

In yet another more particular embodiment, the drug that has a stimulatory effect on osteoclasts is vitamin D, or a vitamin D derivative or mimic thereof.

In yet another more particular embodiment, the estrogen receptor antagonist is selected from the group consisting of raloxifene, bazedoxifene and lasofoxifene.

In yet another more particular embodiment, the bisphosphonate is alendronate, risedronate, ibandronate and zoledronate.

The adenosine A1 receptor antagonist may be administered alone or in combination with one or more of any of the above-noted compounds or agents for treating a bone disease or condition where bone loss or a decrease in bone mass or density is apparent. The adenosine A1 receptor antagonist may be administered with a second adenosine A1 receptor antagonist or with a less selective adenosine receptor antagonist. (ie. one that binds other adenosine receptors in addition to A1, for example A2 or A3) This combination therapy is also contemplated in situations where facilitation of bone repair or replacement is desired such as with bone fractures, bone defects, plastic surgery, dental and other implantations. Combination therapy of the A1 receptor antagonist with a growth hormone, for example, human growth hormone, is also contemplated.

A fifth aspect of the invention provides a pharmaceutical composition comprising an adenosine receptor modulator, in particular, an adenosine receptor antagonist, for inhibiting the differentiation, formation or function of osteoclasts, or for treating, ameliorating, or preventing a bone disease or condition associated with bone loss or low bone mass in a mammal in need thereof, and a pharmaceutically acceptable carrier.

In one embodiment, the adenosine receptor antagonist may be selective for the A1 receptor, or it may be a non-selective adenosine receptor antagonist, which may block or inhibit one or more of the following receptors: A1, A2A, A2B or A3. In a preferred embodiment, the adenosine receptor antagonist is an A1 receptor antagonist.

In another particular embodiment, the pharmaceutical composition comprises the adenosine receptor antagonist alone or in combination with one or more compounds or agents effective for treating a bone disease or bone condition characterized by bone loss or low bone mass or density. The adenosine receptor antagonist and the one or more compounds or agents may be formulated and administered alone or together. The pharmaceutical composition(s) comprising the adenosine receptor antagonist and the one or more compounds or agents may be administered concurrently or sequentially. In another particular embodiment, the one or more compounds or agents effective for treating bone diseases or conditions are selected from antiresorptive drugs, bone-forming agents, estrogen receptor antagonists and drugs that have a stimulatory effect on osteoclasts. The pharmaceutical compositions may be delivered orally or parenterally. They may be delivered via the intravenous route, the intramuscular route, or the subcutaneous route. They may be delivered as an immediate release formulation or as a slow or sustained release formulation.

In another more particular embodiment, the pharmaceutical composition comprising the adenosine receptor antagonist may also contain one or more antiresorptive drugs selected from the group consisting of a bisphosphonate, an estrogen or estrogen analogue, a selective estrogen receptor modulator (SERM) and a calcium source, Tibolone, calcitonin, a calcitriol and hormone replacement therapy.

In yet another more particular embodiment, the pharmaceutical composition comprising the adenosine receptor antagonist may also contain one or more bone-forming agents selected from the group consisting of parathyroid hormone (PTH) or a peptide fragment thereof, PTH-related protein (PTHrp), bone morphogenetic protein, osteogenin, NaF, a $PGE_2$ agonist, a statin, and a RANK ligand (RANKL). In another particular embodiment, the PTH peptide fragment is teriparatide.

In yet another more particular embodiment, the pharmaceutical composition comprising the adenosine receptor antagonist may also contain one or more drugs that have a stimulatory effect on osteoclasts including, but not limited to, vitamin D, or a vitamin D derivative or mimic thereof.

In yet another more particular embodiment, the pharmaceutical composition comprising the adenosine receptor antagonist may also contain one or more estrogen receptor antagonists selected from the group consisting of raloxifene, bazedoxifene and lasofoxifene.

In yet another more particular embodiment, the pharmaceutical composition comprising the adenosine receptor antagonist may also contain one or more of the bisphosphonates selected from the group consisting of alendronate, risedronate, ibandronate and zoledronate.

Various adenosine receptor modulators, including agonists or antagonists/inhibitors, including specific A1 receptor inhibitors, have been identified and are known in the art. Examples of A1 receptor inhibitors in the art include but are not limited to those shown in Table 1 and in U.S. Pat. Nos. 6,495,687; 6,489,332; 6,117,998; 6,605,601; 5,840,729; 5,786,360; 2005/0245546; 2005/0119258; 2005/0059683; 2005/0187226; 2003/0220358; 2003/0045536; 2002/0111333; and 2002/0082269, as well as those shown in FIG. 3.

Other objects and advantages will become apparent to those skilled in the art from a review of the following description which proceeds with reference to the following illustrative drawings.

*, p=0.446 vs cultures on day 6 with M-CSF and RANKL. Similar results were obtained in three independent experiments.

Figure 6:
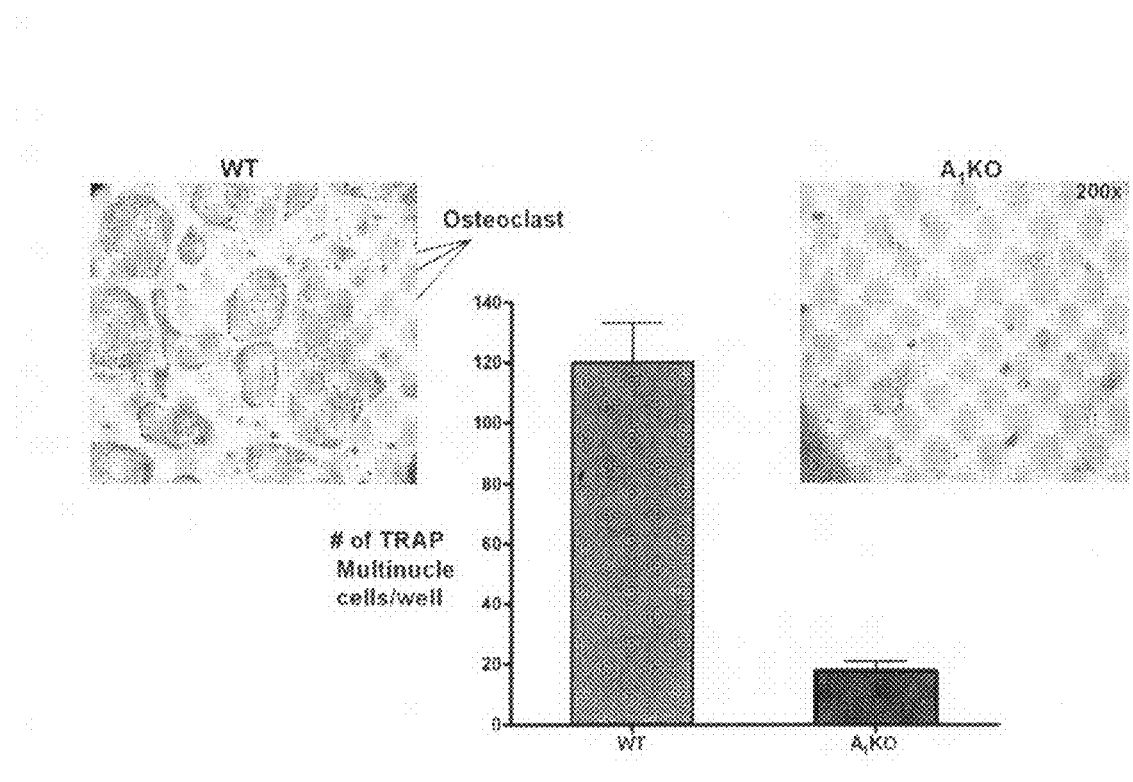

FIG. 6. Diminished Osteoclast Formation by Splenocytes from $A_1$ Receptor Knockout Mice. Splenocytes of 6- to 8-wk-old $A_1$WT female mice and $A_1$KO mice were incubated in 24-well plates ($3 \times 10^5$ cells/well) in the presence of M-CSF and RANKL (30 ng/ml). After 7 days cells were fixed and stained for TRAP, and the number of TRAP-positive MNCs per well was scored. (Similar results were obtained in three independent experiments).

Figure 7:
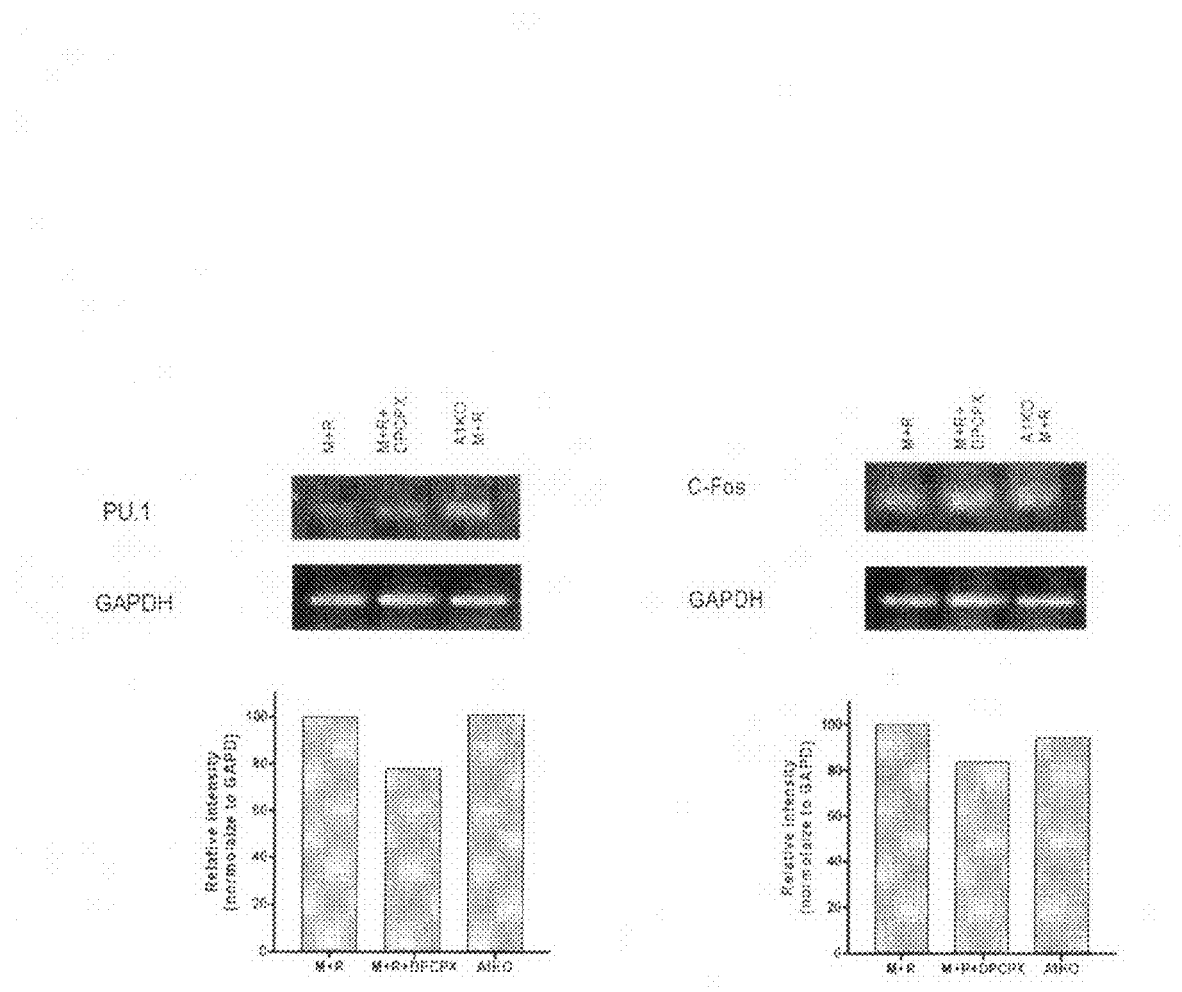

FIG. 7. Effect of DPCPX on the expression of PU.1 and c-Fos mRNA. Osteoclast precursors were cultured in the presence of M-CSF and RANKL (30 ng/ml) with or without DPCPX (1 µM/ml) in $A_1$WT and from $A_1$KO mice for 7 days. Total RNA was extracted and subjected to RT-PCR analysis. The relative intensities of PU.1 and c-Fos were analyzed by densitometry and are represented in the form of a bar graph. Similar results were obtained in two independent experiments.

Figure 8:
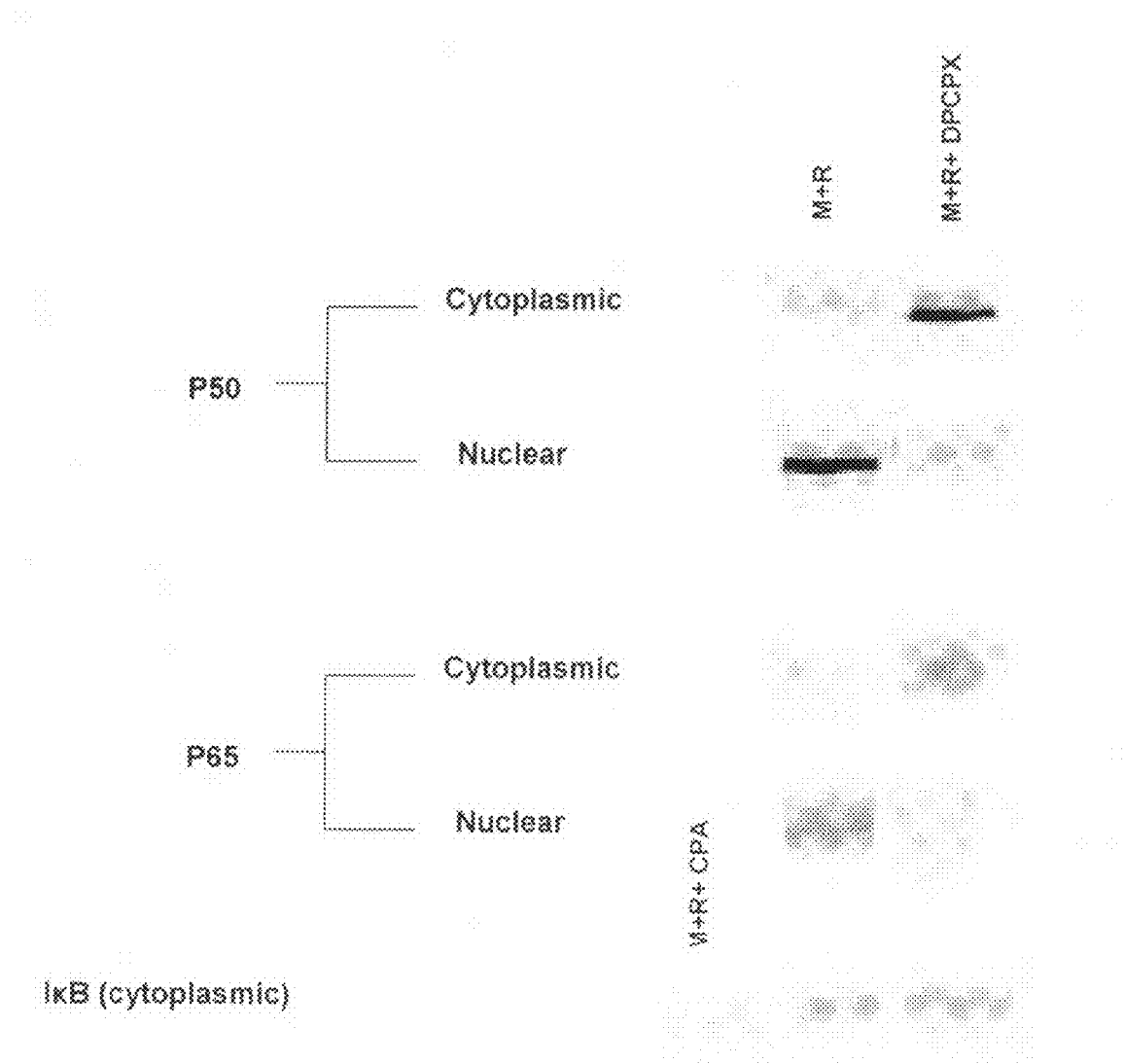

FIG. 8. Effect of DPCPX on RANKL-induced NF-κB signaling. A, Osteoclast precursors were preincubated for 3 days in the presence of M-CSF and RANKL (30 ng/ml) with or without DPCPX (1 µM/ml) as indicated. Cells were lysed, and cytoplasmic and nuclear fractions were separated. Cytosols were analyzed for IκBα and p50 and p65 NF-κB, and nuclear extracts were analyzed for p50 and p65 NF-κB by immunoblots. Results are representative of three independent experiments.

Figure 9:
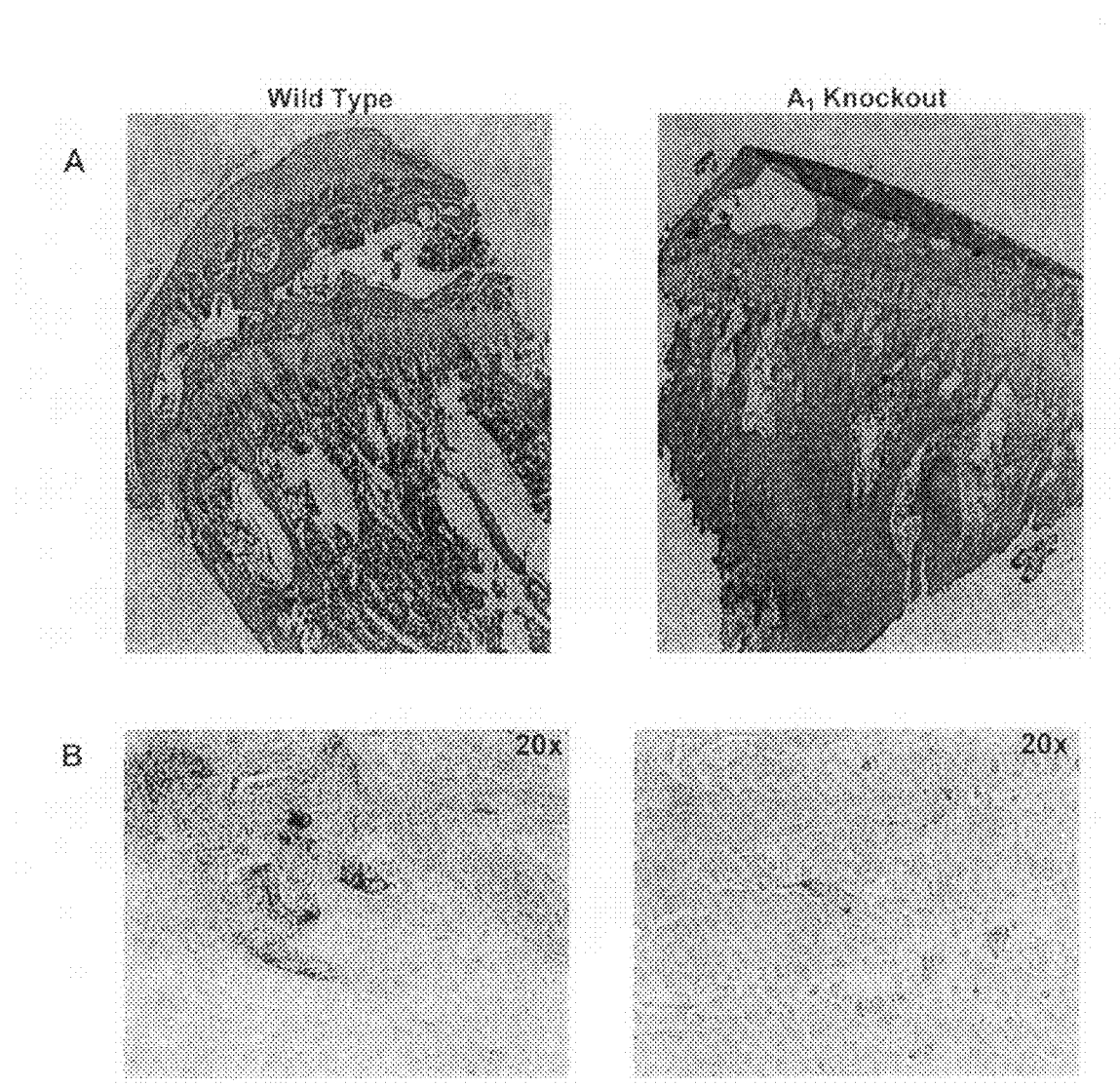

FIG. 9. Severe osteopetrosis in the presence of TRAP⁺ osteoclasts in $A_1$KO mice. (A) H & E staining (B) Cathepsin K staining. Presence of multinucleated Cathepsin K⁺ osteoclasts in $A_1$KO mice. Most $A_1$KO osteoclasts are withdrawn from the bone surface, whereas osteoclasts in wild type mice are attached to the bone. Magnification 400×

Figure 10:
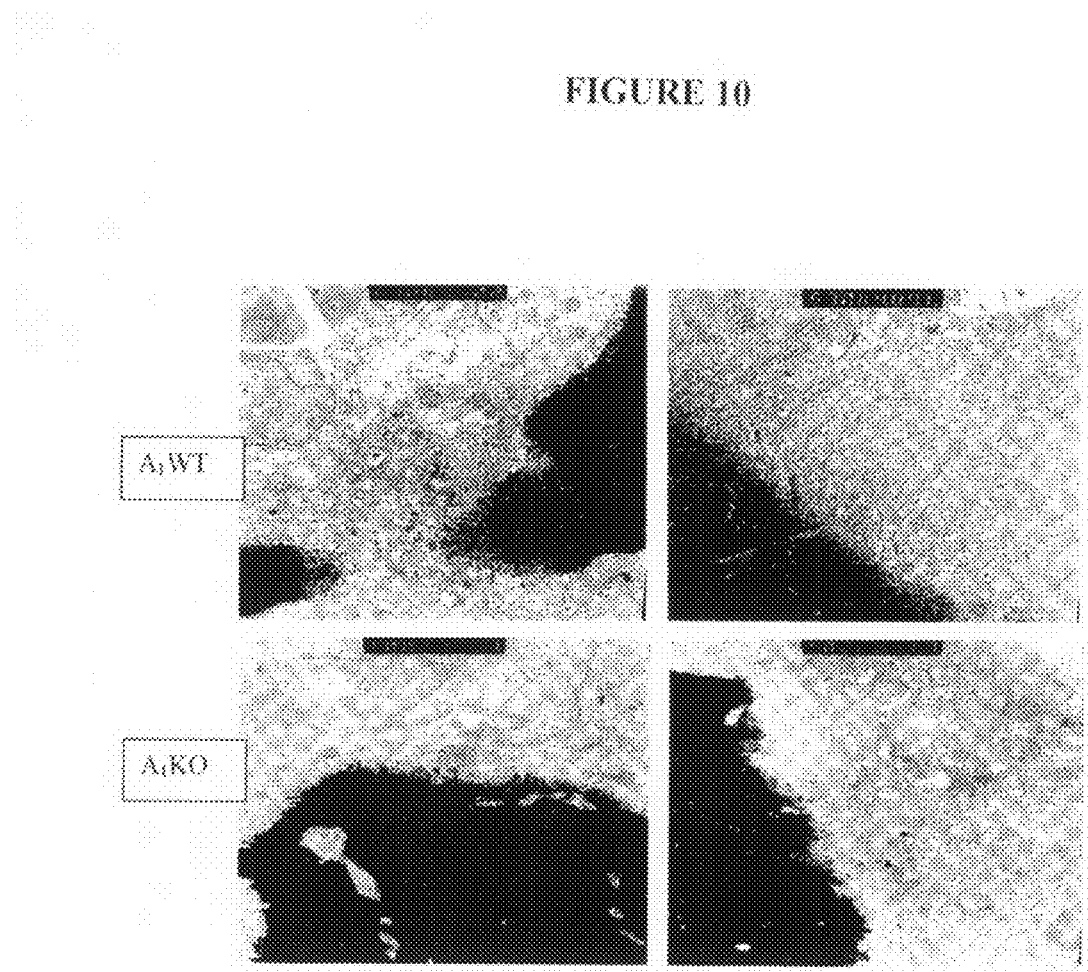

FIG. 10. Electron microscopy of osteoclasts in $A_1$KO and $A_1$WT mice. (A) The osteoclast in the $A_1$WT mice shows elaborate membrane folding in the brush border and extensive bone resorption and has a partial and disorganized ruffled border. (B) The Osteoclasts from the $A_1$KO mice shows very little membrane folding and much less bone resorption. There is no evidence of activation or mineral resorption, the cell forms no attachment zone or ruffled border and is in limited contact with the underlying bone. However, on most of the bone surface covered, there is no ruffled border formation and no bone resorption.

Figure 11:
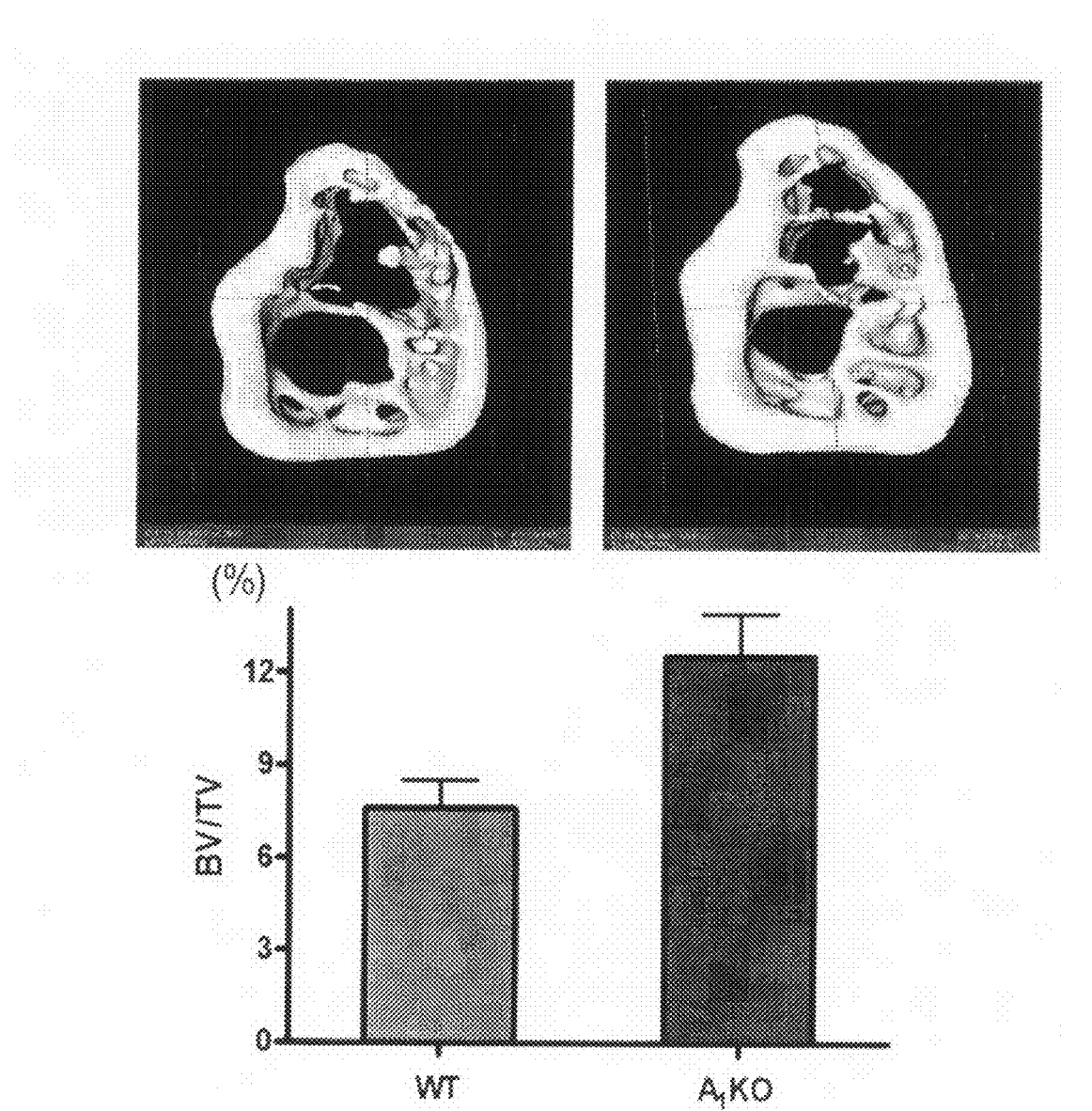

FIG. 11. $A_1$ knockout mice have increased bone mass. Total mouse BMD and BMC assessed by dual X-ray absorptiometry and by Micro CT in $A_1$ knockout (KO) mice and wild-type (WT) littermates.

Figure 12:
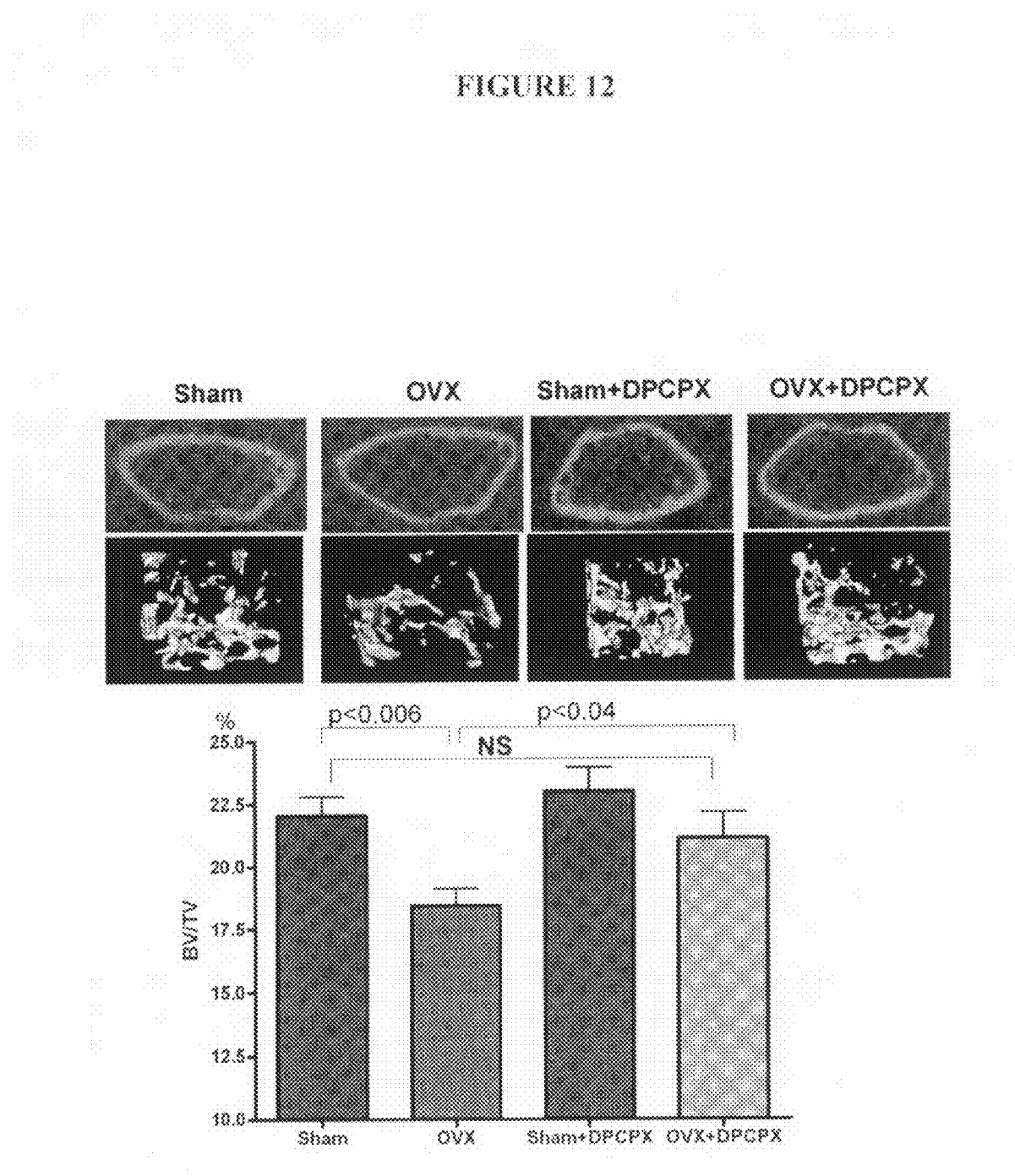

FIG. 12. Effects of the $A_1$R Antagonist DPCPX on Bone Loss Due to Ovariectomy. Oral administration of an $A_1$ Receptor Antagonist (DPCPX, 50 mg/kg/d) prevents ovariectomy-induced bone loss effects of DPCPX on trabecular bone volume (bone volume/total volume) in sham-operated (Sham) and ovariectomized (OVX) C57BL/6 mice. Data are expressed as percent change relative to sham-operated vehicle-treated control mice.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Antagonist" refers to an agent that down-regulates (e.g., suppresses or inhibits) at least one bioactivity of a protein. An "antagonist" or an agent that "antagonizes" may be a compound which inhibits or decreases the interaction between a protein and another molecule, e.g., a target peptide or enzyme substrate. An antagonist may also be a compound that down-regulates expression of a gene or which reduces the amount of expressed protein present. Methods for assessing the ability of an agent to "antagonize" or "inhibit" an adenosine receptor are known to those skilled in the art.

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (eg. to treat or prevent bone disease, or to modulate osteoclast differentiation), but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

A "small molecule" refers to a composition that has a molecular weight of less than 3 kilodaltons (kDa), and preferably less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, and preferably less than 1.5 kilodaltons, and more preferably less than about 1 kDa.

"Diagnosis" or "screening" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g sequentially. The desired result can be either a subjective relief of one or more symptoms or an objectively identifiable improvement in the recipient of the dosage.

"Differentiate" or "differentiation" as used herein, generally refers to the process by which precursor or progenitor cells differentiate into specific cell types. In the matter of the present invention, the term refers to the process by which pre-osteoclasts become osteoclasts. Differentiated cells can be identified by their patterns of gene expression and cell surface protein expression. As used herein, the term "differentiate" refers to having a different character or function from the original type of tissues or cells. Thus, "differentiation" is the process or act of differentiating. The term "Osteoclast Differentiation" refers to the process whereby osteoclast precursors in the bone marrow become functional osteoclasts.

"Modulation" or "modulates" or "modulating" refers to up regulation (i.e., activation or stimulation), down regulation (i.e., inhibition or suppression) of a response, or the two in combination or apart. As used herein, an adenosine receptor "modulator" or "modulating" compound or agent is a compound or agent that modulates at least one biological marker or biological activity characteristic of osteoclasts and bone formation. The term "modulating" as related to osteoclast differentiation, refers to the ability of a compound or agent to exert an effect on precursors to osteoclasts, or to alter the expression of at least one gene related to osteoclastogenesis. For example, expression of the following genes is modulated during osteoclastogenesis: DC-Stamp, tartrate resistant alkaline phosphatase (TRAP), cathepsin K, calcitonin receptor, □3 integrin.

As used herein, the term "candidate compound" or "test compound" or "agent" or "test agent" refers to any compound or molecule that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted. In the present invention, the treatments using the agents described may be provided to slow or halt bone loss, or to increase the amount or quality of bone density. Most preferably, the treating is for the purpose of reducing or diminishing the symptoms or progression of a disease or disorder of the bone. Treating as used herein also means the administration of the compounds for increasing the bone density or for modulating osteoclastogenesis in individuals. Furthermore, in treating a subject, the compounds of the invention may be administered to a subject already suffering from loss of bone mass or other bone disease as provided herein or to prevent or inhibit the occurrence of such condition.

"Subject" or "patient" refers to a mammal, preferably a human, in need of treatment for a condition, disorder or disease.

"Osteoclastogenesis" refers to osteoclast generation, which is a multi-step process that can be reproduced in vitro. Earlier in vitro osteoclastogenesis systems comprised mixtures of stromal or osteoblastic cells together with osteoclast precursors from bone marrow (Suda, T., Jimi, E., Nakamura, I., and Takahashi, N. (1997) *Methods Enzymol.* 282, 223-235; David, J. P., Neff, L., Chen, Y., Rincon, M., Home, W. C., and Baron, R. (1998) *J. Bone Miner. Res.* 13, 1730-1738). These systems utilized 1α,25-dihydroxyvitamin $D_3$ to stimulate stromal/osteoblastic cells to produce factors that support osteoclast formation More recent models utilize bone marrow cells cultured with soluble forms of the cytokines M-CSF (macrophage-colony stimulating factor) and a soluble form of RANKL (receptor activator of nuclear factor κB ligand) (Lacey, D. L., Timms, E., Tan, H. L., Kelley, M. J., Dunstan, C. R., Burgess, T., Elliott, R., Colombero, A., Elliott, G., Scully, S., Hsu, H., Sullivan, J., Hawkins, N., Davy, E., Capparelli, C., Eli, A., Qian, Y. X., Kaufman, S., Sarosi, I., Shalhoub, V., Senaldi, G., Guo, J., Delaney, J., and Boyle, W. J. (1998) *Cell* 93, 165-176; Shevde, N. K., Bendixen, A. C., Dienger, K. M., and Pike, J. W. (2000) *Proc. Natl. Acad. Sci. U.S.A.* 97, 7829-7834). These two cytokines are now recognized as the major factors from stromal cells that support osteoclastogenesis (Takahashi, N., Udagawa, N., and Suda, T. (1999) *Biochem. Biophys. Res. Commun.* 256, 449-455). Thus, their addition to the culture medium overcomes the need for stromal cells.

"Osteoclast precursor" refers to a cell or cell structure, such as a pre-osteoclast, which is any cellular entity on the pathway of differentiation between a macrophage and a differentiated and functional osteoclast. The term osteoclast includes any osteoclast-like cell or cell structure which has differentiated fully or partially from a macrophage, and which has osteoclast character, including but not limited to positive staining for tartrate-resistant acid phosphatase (TRAP), but which is not a fully differentiated or functional osteoclast, including particularly aberrantly differentiated or non functional osteoclasts or pre-osteoclasts.

"Osteoclast culture" refers to any in vitro or ex vivo culture or system for the growth, differentiation and/or functional assessment of osteoclasts or osteoclast precursors, whether in the absence or presence of other cells or cell types, for instance, but not limited to, osteoblasts, macrophages, hematopoietic or stromal cells.

"Osteoclast function", as used herein, refers to bone resorption and the processes required for bone resorption.

An "amount sufficient to inhibit osteoclast differentiation, formation or function" refers to the amount of the A1 receptor antagonist sufficient to block either the differentiation, the formation or the function of osteoclasts, more particularly, an amount ranging from about 0.1 nM to about 10 μM, or more preferentially from about 0.1 nM to about 5 μM, and most preferentially from about 0.1 nM to about 1 μM in vitro. In vivo amounts of the A1 receptor antagonist sufficient to block either the differentiation, the formation or the function of osteoclasts may range from about 0.1 mg/Kg of body weight per day to about 200 mg/Kg of body weight per day in vivo, or more preferentially from about 1 mg/Kg to about 100 mg/Kg, and most preferentially from about 25 mg/Kg to about 50 mg/Kg of body weight per day in vivo. It is to be understood that the dose, when administered in vivo, may vary depending on the clinical circumstances, such as route of administration, age, weight and clinical status of the subject in which inhibition of osteoclast differentiation, formation or function is desired.

In a specific embodiment, the term "about" means within 20%, preferably within 10%, and more preferably within 5%.

An "effective amount" or a "therapeutically effective amount" is an amount sufficient to decrease or prevent the symptoms associated with the conditions disclosed herein, including diseases affecting the bone, or conditions that result in bone loss or in a decrease in bone mass or density, such as that which occurs in osteoporosis or other related conditions contemplated for therapy with the compositions of the present invention. For example, an "effective amount" for therapeutic uses is the amount of the composition comprising an active compound herein required to provide a clinically significant increase in healing rates in fracture repair; reversal or inhibition of bone loss in osteoporosis; prevention or delay of onset of osteoporosis; stimulation and/or augmentation of bone formation in fracture non-unions and distraction osteogenesis; increase and/or acceleration of bone growth into prosthetic devices; repair or prevention of dental defects; or treatment or inhibition of other bone loss conditions, diseases or defects, including but not limited to those discussed herein above. Such effective amounts will be determined using routine optimization techniques and are dependent on the particular condition to be treated, the condition of the subject, the route of administration, the formulation, and the judgment of the practitioner and other factors evident to those skilled in the art. The dosage required for the compounds of the invention (for example, in osteoporosis where an increase in bone formation and/or reduction in bone loss is desired) is manifested as that which induces a statistically significant difference in bone mass or bone loss between treatment and control groups. This difference in bone mass or bone loss may be seen, for example, as at least 1-2%, or any clinically significant increase in bone mass or reduction in bone loss in the treatment group. Other measurements of clinically significant increases in healing may include, for example, an assay for the N-terminal propeptide of Type I collagen, tests for breaking strength and tension, breaking strength and torsion, 4-point bending, increased connectivity in bone biopsies and other biomechanical tests well known to those skilled in the art. General guidance for treatment regimens may be obtained from experiments carried out in vitro or in animal models of the disease of interest. The "effective amount" or "therapeutically effective amount" may range from about 1 mg/Kg to about 200 mg/Kg in vivo, or more preferentially from about 10 mg/Kg to about 100 mg/Kg, and most preferentially from about 25 mg/Kg to about 50 mg/Kg in vivo.

As used herein, the term "disease or condition characterized by bone loss" is meant to refer to diseases, conditions, disorders and syndromes which have as a symptom or pathology a decrease in bone mass or density. Examples of diseases characterized by bone loss include osteoporosis, Paget's disease, metastatic bone disease, rheumatoid arthritis and periodontal bone disease. Individuals who have a disease characterized by bone loss can be identified by those having ordinary skill in the art by well known diagnostic means and criteria. Individuals who are susceptible to a disease characterized by bone loss can be identified by those having ordinary skill in the art based upon family medical history and/or the presence of genetic markers or genes associated with a disease characterized by bone loss.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Binding compounds can also be characterized by their effect on the activity of the target molecule. Thus, a "low activity" compound has an inhibitory concentration (IC50) (for inhibitors or antagonists) or effective concentration (EC50) (applicable to agonists) of greater than 1 μM under standard conditions. By "very low activity" is meant an IC50 or EC50 of above 100 μM under standard conditions. By "extremely low activity" is meant an IC50 or EC50 of above 1 mM under standard conditions. By "moderate activity" is meant an IC50 or EC50 of 200 nM to 1 μM under standard conditions. By "moderately high activity" is meant an IC50 or EC50 of 1 nM to 200 nM. By "high activity" is meant an IC50 or EC50 of below 1 nM under standard conditions. The IC50 (or EC50) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a bone disease or condition characterized by low bone mass or density. An individual having one or more of these risk factors has a higher probability of developing a bone disease than an individual without these risk factors.

"Prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

General Description

The invention relates to the unexpected finding that the blocking of the adenosine A1 receptor with agents that are antagonists of the A1 receptor leads to or results in inhibition of osteoclast differentiation, formation, or function. As such, these antagonists may be used to treat a subject having a condition characterized by bone loss or low bone density. Such bone diseases or conditions include, but are not limited to osteoporosis, juvenile osteoporosis, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, periodontal bone loss, age-related loss of bone mass, osteotomy and bone loss associated with prosthetic ingrowth, other forms of osteopenia, and in other conditions where facilitation of bone repair or replacement is desired such as bone fractures, bone defects, plastic surgery, dental and other implantations. Likewise, these A1 receptor antagonists may be used to increase bone mass or may ameliorate loss of bone mass in any of these conditions. It was determined that adenosine $A_1$ receptor occupancy is critical in the formation of osteoclasts by murine splenocytes incubated with macrophage colony stimulating factor (M-CSF) and receptor activator of NFkB ligand (RANKL) in vitro. In the absence of adenosine $A_1$ receptors mice appear to develop osteopetrosis. These results suggest that adenosine $A_1$ receptor antagonists may be useful in the treatment of osteoporosis, prosthetic joint loosening and other conditions in which osteoclasts play a pathogenic role (eg Paget's Disease).

Adenosine, a potent endogenous physiological mediator, regulates a wide variety of physiological processes via interaction with one or more of four G protein-coupled receptors (A1,A2A,A2B, and A3), expressed on many cell types, including neutrophils, macrophages, fibroblasts, and endothelial cells. Because adenosine A1 receptors promote, and adenosine A2A receptors inhibit the formation of giant cells from peripheral blood monocytes in vitro it was determined whether adenosine, acting through one or another of these receptors, regulated the formation of osteoclasts It was determined that osteoclast formation is reduced by adenosine A2A receptor occupancy. More strikingly, it was observed that adenosine $A_1$ receptor occupancy is critically required for osteoclast formation since pharmacologic blockade of these receptors completely inhibits the formation of osteoclasts in vitro. Furthermore, macrophages from mice lacking adenosine A1 receptors do not undergo osteoclast formation. Moreover, it was determined that A1 knockout mice appear to have a marked diminution in the number of osteoclasts in the bone associated with diminished bone remodeling (osteopetrosis).

Selecting Compounds or Agents

Figure 3:
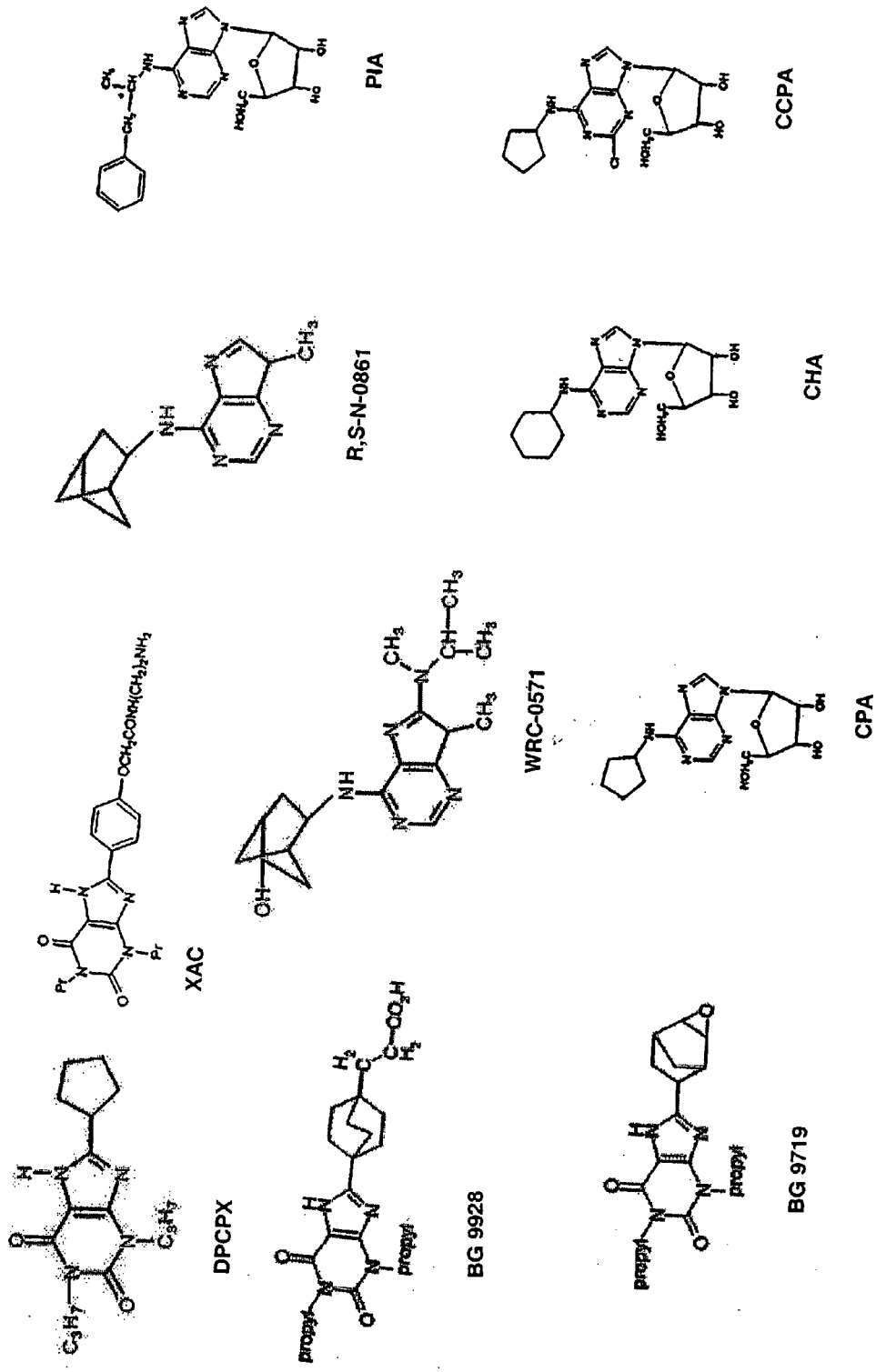
FIG. 3. Structures of exemplary adenosine receptor antagonists.

Various adenosine receptor antagonists, including those specific for the A1 receptor, have been identified and are known in the art. Examples of A1 receptor antagonists in the art include but are not limited to: xanthine and non-xanthine antagonists described in U.S. Pat. Nos. 6,495,687; 6,489,332; 6,117,998; 6,605,601; 5,840,729; 5,786,360; 2005/0245546; 2005/0119258; 2005/0059683; 2005/0187226; 2003/0220358; 2003/0045536; 2002/0111333; and 2002/0082269 and in Table 1 and FIG. 3. Particularly preferred are compounds or agents which are selective for the A1 adenosine receptor. The invention provided herein includes the use of these inhibitors for the modulation, in particular, inhibition of osteoclast differentiation or formation or function and treatment of bone disease, including for instance osteoporosis, juvenile osteoporosis, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, periodontal bone loss, age-related loss of bone mass, osteotomy and bone loss associated with prosthetic ingrowth, other forms of osteopenia, and in other conditions where facilitation of bone repair or replacement is desired such as bone fractures, bone defects, plastic surgery, dental and other implantations.

Based on this discovery, the present invention further provides for a method of discovery of agents or compounds which modulate osteoclastogenesis and for use in modulating the differentiation and/or function of osteoclasts through their ability to block or antagonize an adenosine receptor, eg A1. Thus, in one embodiment, methods are provided for screening agents or compounds which inhibit the adenosine A1 receptor, thereby modulating the differentiation and/or function of osteoclasts.

In one embodiment, agents that interact with (e.g., bind to) and block or antagonize an adenosine receptor, in particular, A1 (e.g. a functionally active fragment), are identified in a cell-based assay system. In accordance with this embodiment, cells expressing an adenosine receptor, a fragment of an adenosine receptor, an adenosine receptor related polypeptide, or a binding fragment thereof, are contacted with a candidate compound or a control compound and the ability of the candidate compound to interact with the A1 receptor or fragment thereof is determined. Alternatively, the ability of a candidate compound to compete for binding with a known ligand or compound known to bind the A1 receptor is measured. If desired, this assay may be used to screen a plurality (e.g. a library) of candidate compounds. The cell, for example, can be of prokaryotic origin (e.g., *E. coli*) or eukaryotic origin (e.g., yeast, insect or mammalian). Further, the cells can express the A1 receptor endogenously or be genetically engineered to express the A1 receptor, a binding fragment or an A1 receptor fusion protein. In some embodiments, the A1 receptor or fragment thereof, or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between the A1 receptor and a candidate compound. The ability of the candidate compound to interact directly or indirectly with a A1 receptor or binding fragment thereof or a fusion protein or to modulate the activity of the A1 receptor can be determined by methods known to those of skill in the art. For example, the interaction or modulation by a candidate compound can be determined by flow cytometry, a scintillation assay, immunoprecipitation or western blot analysis, based on the present description, or by a competitive radioreceptor assay.

Another method includes the exposure of an osteoclast culture or osteoclast precursor culture to a candidate A1 modulator (inhibitor), and determining the duration and intensity of the response (for instance, the differentiation and/or function of the osteoclast in culture) in the presence of the candidate compound and comparing the duration and intensity to that response in the absence of the candidate compound or in the presence of a known A1 inhibitor. The comparison step of the invention can be preferably performed directly, i.e., by comparing the culture's response to the candidate A1 modulator to that of a known A1 modulator in a contemporaneous parallel culture. Alternatively, the comparison can be made with a historical control showing differentiation or an effect on osteoclast formation or function that is comparable to that observed under the same conditions with the culture and a known A1 modulator.

In an alternative embodiment, the comparison is performed longitudinally. Replicate cultures, i.e., at least duplicate, are established and the candidate compound is introduced into the cultures. The response of the cultures at time points that are shortly after the introduction and before and at or after some time (for instance one hour) following the introduction is determined. An A1 modulator can be identified by the persistence of the response by comparison to a contemporaneous control.

An exemplary method of screening osteogenic compounds, particularly compounds which modulate osteoclast differentiation and/or function, comprises selecting a compound that modulates, particularly inhibits, the A1 receptor by performing an osteoclast assay with said compound and determining the result of the osteoclast assay, wherein a result indicates that the tested compound possesses osteogenic potential.

Briefly, selecting the compounds that interact with or bind to an A1 receptor or otherwise inhibit or block the A1 receptor may be performed in multiple ways. The compounds may first be chosen based on their structural and functional characteristics, using one of a number of approaches known in the art. For instance, homology modeling can be used to screen small molecule libraries in order to determine which molecules would be candidates to interact with A1 thereby selecting plausible targets. See neogenesis.com for a commercially available screening of compounds using multiple different approaches such as an automated ligand identification system and quantized surface complementarity. The compounds to be screened can include both natural and synthetic ligands. Furthermore, any desired compound may be examined for its ability to interact with or bind to A1 receptor including as described below.

Binding to or interaction with A1 or other adenosine receptors may be determined by performing an assay such as, e.g., a binding assay between a desired compound and an adenosine receptor. In one aspect, this is done by contacting said compound to an adenosine receptor and determining its dissociation rate. Numerous possibilities for performing binding assays are well known in the art. The indication of a compound's ability to bind to adenosine receptor is determined, e.g., by a dissociation rate, and the correlation of binding activity and dissociation rates is well established in the art. For example, the assay may be performed by radio-labeling a reference compound, or other suitable radioactive marker, and incubating it with the cell bearing an adenosine receptor, in particular, A1. Test compounds are then added to these reactions in increasing concentrations. After optimal incubation, the reference compound and receptor complexes are separated, e.g., with chromatography columns, and evaluated for bound $^{125}$I-labeled peptide with a gamma ($\gamma$) counter. The amount of the test compound necessary to inhibit 50% of the reference compound's binding is determined. These values are then normalized to the concentration of unlabeled reference compound's binding (relative inhibitory concentration $(RIC)^{-1}$=concentration$_{test}$/concentration$_{reference}$). A small $RIC^{-1}$ value indicates strong relative binding, whereas a large $RIC^{-1}$ value indicates weak relative binding. See, for example, Latek et al., Proc. Natl. Acad. Sci. USA, Vol. 97, No. 21, pp. 11460-11465, 2000. An adenosine A1 receptor antagonist mimic may be computationally evaluated and designed by means of a series of steps in which chemical groups or fragments are screened and selected for their ability to associate with the individual binding pockets or interface surfaces of the protein (e.g. the A1 receptor). One skilled in the art may employ one of several methods to screen chemical groups or fragments for their ability to associate with the adenosine receptor. This process may begin by visual inspection of, for example, the protein/protein interfaces or the binding site on a computer screen based on the available crystal complex coordinates of the A1 receptor, including a protein known to interact with A1 Selected fragments or chemical groups may then be positioned in a variety of orientations, or docked, at an individual surface of A1 that participates in a protein/protein interface or in the binding pocket. Docking may be accomplished using software such as QUANTA and SYBYL, followed by energy minimization and molecular dynamics with standard molecular mechanics forcefields, such as CHARMM and AMBER (AMBER, version 4.0 (Kollman, University of California at San Francisco © 1994); QUANTA/CHARMM (Molecular Simulations, Inc., Burlington, Mass., ©1994)). Specialized computer programs may also assist in the process of selecting fragments or chemical groups. These include: GRID (Goodford, 1985, J. Med. Chem. 28:849-857), available from Oxford University, Oxford, UK; MCSS (Miranker & Karplus, 1991, Proteins: Structure, Function and Genetics 11:29-34), available from Molecular Simulations, Burlington, Mass.; AUTODOCK (Goodsell & Olsen, 1990, Proteins: Structure, Function, and Genetics 8:195-202), available from Scripps Research Institute, La Jolla, Calif.; and DOCK (Kuntz et al., 1982, J. Mol. Biol. 161:269-288), available from University of California, San Francisco, Calif. Once suitable chemical groups or fragments that bind to A1 have been selected, they can be assembled into a single compound or inhibitor. Assembly may proceed by visual inspection of the relationship of the fragments to each other in the three-dimensional image displayed on a computer screen in relation to the structure coordinates thereof. This would be followed by manual model building using software such as QUANTA or SYBYL. Useful programs to aid one of skill in the art in connecting the individual chemical groups or fragments include: CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182-196), available from the University of California, Berkeley, Calif.; 3D Database systems such as MACCS-3D (MDL Information Systems, San Leandro, Calif.). This area is reviewed in Martin, 1992, J. Med. Chem. 35:2145-2154); and HOOK (available from Molecular Simulations, Burlington, Mass.). Instead of proceeding to build an adenosine receptor antagonist mimic, in a step-wise fashion one fragment or chemical group at a time, as described above, such compounds may be designed as a whole or 'de novo' using either an empty binding site or the surface of a protein that participates in protein/protein interactions or optionally including some portion(s) of a known activator(s). These methods include: LUDI (Bohm, 1992, J. Comp. Aid. Molec. Design 6:61-78), available from Molecular Simulations, Inc., San Diego, Calif.; LEGEND (Nishibata & Itai, 1991, Tetrahedron 47:8985), available from Molecular Simulations, Burlington, Mass.; and LeapFrog (available from Tripos, Inc., St. Louis, Mo.). Other molecular modeling techniques may also be employed in accordance with this invention. See, e.g., Cohen et al., 1990, J. Med. Chem. 33:883-894. See also, Navia & Murcko, 1992, Current Opinions in Structural Biology 2:202-210.

Once a compound has been designed by the above methods, the efficiency with which that compound may bind to or interact with the adenosine receptor protein may be tested and optimized by computational evaluation. Inhibitors may interact with the receptor in more than one conformation that is similar in overall binding energy. In those cases, the deformation energy of binding is taken to be the difference between the energy of the free compound and the average energy of the conformations observed when the inhibitor binds to the receptor protein.

A compound selected for binding to A1 or other adenosine receptors may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the inhibitor and the receptor protein when the mimic is bound to it preferably make a neutral or favorable contribution to the enthalpy of binding. Specific computer software is available in the art to evaluate compound deformation energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco ©1994); QUANTA/CHARMM (Molecular Simulations, Inc., Burlington, Mass., ©1994); and Insight II/Discover (Biosym Technologies Inc., San Diego, Calif., ©1994). These programs may be implemented, for instance, using a computer workstation, as are well-known in the art. Other hardware systems and software packages will be known to those skilled in the art.

Once an adenosine A1 receptor modulating compound (preferably an inhibitor) has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to A1 by the same computer methods described in detail above.

Performing Osteoclast and Bone Formation Assays and Determining Results

Once a compound that binds to A1 and preferably inhibits or blocks the A1 adenosine receptor is selected, it is then tested for its ability to modulate the differentiation or function of osteoclasts. There are multiple osteoclast culture systems or methods and bone formation assays that can be used successfully to screen potential osteogenic compounds of this invention. See, e.g., U.S. Pat. No. 6,080,779.

One osteoclast culture for use in screening is a neonatal mouse calvaria assay. Briefly, four days after birth, the front and parietal bones of neonatal mouse pups (e.g., ICR Swiss white mice) are removed by microdissection and split along the sagittal suture. The bones are then incubated in a specified medium, wherein the medium contains either test or control compounds. Following the incubation, the bones are removed from the media, and fixed in 10% buffered formalin, decalcified in EDTA, processed through graded alcohols, and embedded in paraffin wax. Sections of the calvaria are prepared and assessed using histomorphometric analysis of bone formation and bone resorption. Bone changes are measured on sections. Osteoblasts and osteoclasts are identified by their distinctive morphology.

In addition to this assay, the effect of compounds on murine calvarial bone growth can also be tested in vivo. In one such example of this screening assay, young male mice (e.g., ICR Swiss white mice), aged 4-6 weeks are employed, using about 4-5 mice per group. Briefly, the test compound or the appropriate control is injected into subcutaneous tissue over the right calvaria of normal mice. The mice are sacrificed (after allowing for bone growth or loss to occur, e.g. on day 14), and net bone growth is measured by histomorphometric means. Bone samples are cleaned from adjacent tissues and fixed in 10% buffered formalin, decalcified, processed through graded alcohols, and embedded in paraffin wax. Sections of the calvaria are prepared, and representative sections are selected for histomorphometric assessment of the effects of bone formation and bone resorption. In one embodiment, sections are measured by using a camera lucida attachment to trace directly the microscopic image onto a digitizing plate. Bone changes are measured on sections over adjacent 1×1 mm fields on both the injected and noninjected sides of calvaria. New bone may be identified by those skilled in the art by its characteristic tinctorial features, and osteoclasts and osteoblasts may be identified by their distinctive morphology or other suitable marker recognized by the skilled artisan. Histomorphometry software (OsteoMeasure, Osteometrix, Inc., Atlanta) can be used to process digitized input to determine cell counts and measure areas or perimeters.

Additional exemplary in vivo assays include dosing assays in intact animals, including dosing assays in acute ovariectomized (OVX) animals and assays in chronic OVX animals. Prototypical dosing in intact animals may be accomplished by subcutaneous, intraperitoneal or oral administration, and may be performed by injection, sustained release or other delivery techniques. The time period for administration of test compound may vary (for instance, 14 days, 28 days, as well as 35 days or longer may be appropriate).

As an example, in vivo oral or subcutaneous dosing assay may be performed as described: For example, about 70 three-month-old female Sprague-Dawley rats are weight-matched and divided into treatment groups, with at least several animals in each group to aid in statistical analysis. This includes a baseline control group of animals sacrificed at the initiation of the study; a control group administered vehicle only; a PBS or saline-treated control group; and a positive group administered a compound known to enhance net bone formation. Three dosage levels of the test compound are administered to the remaining groups. Test compound, saline, and vehicle are administered (e.g. once per day) for a number of days (for instance at least 14 days, 28 days, or 35 day—wherein an effect is expected in the positive group). All animals are injected calcein nine days and two days before sacrifice (to ensure proper labeling of newly formed bone). Weekly body weights are determined. At the end of the period of compound administration, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol or 10% formalin for evaluation, for instance as performed by peripheral quantitative computed tomography (pQCT; Ferretti, J, Bone, 17: 353S-364S, 1995), dual energy X-ray absorptiometry (DEXA; Laval-Jeantet A. et al., Calcif Tissue Intl, 56:14-18, 1995, and Casez J. et al., Bone and Mineral, 26:61-68, 1994) and/or histomorphometry. The effect of test compounds on bone remodeling or net bone formation, including bone loss and osteoclast function can thus be evaluated.

Test compounds can also be assayed in acute ovariectomized animals. Such assays may also include an estrogen-treated group as a control. An example of the test in these animals is briefly described: In a typical study, 80 three-month-old female Sprague-Dawley rats are weight-matched and divided into treatment groups, with at least several animals in each group. This includes a baseline control group of animals sacrificed at the initiation of the study; three control groups (sham OVX and vehicle only, OVX and vehicle only, and OVX and PBS only); and a control OVX group that is administered a compound known to block or reduce bone resorption or enhance bone formation (including an anti-resorptive or anabolic compound). Different dosage levels of the test compound are administered to remaining groups of OVX animals. Since ovariectomy induces hyperphagia, all OVX animals are pair-fed with sham OVX animals throughout the study. Test compound, positive control compound, PBS or saline or vehicle alone is administered orally or subcutaneously (e.g., once per day) for the treatment period. As an alternative, test compounds can be formulated in implantable pellets that are implanted, or may be administered orally, such as by gastric gavage. All animals are injected with calcein (Flourescein-Methylene-iminodiacetic acid) nine days and two days before sacrifice. Weekly body weights are determined. At the end of the treatment cycle, the animals blood and tissues are processed as described above.

Test compounds may also be assayed in chronic OVX animals. Briefly, six month old female, Sprague-Dawley rats are subjected to sham surgery (sham OVX), or ovariectomy (OVX) at the beginning of the experiment, and animals are sacrificed at the same time to serve as baseline controls. Body weights are monitored weekly. After approximately six weeks or more of bone depletion, sham OVX and OVX rats are randomly selected for sacrifice as depletion period controls. Of the remaining animals, 10 sham OVX and 10 OVX rats are used as placebo-treated controls. The remaining animals are treated with 3 to 5 doses of test compound for a period of 35 days. As a positive control, a group of OVX rats can be treated with a known anabolic or anti-resorptive agent in this model, such as bisphosphonate, a calcitonin, a calcitriol, an estrogen, selective estrogen receptor modulators (SERM's) and a calcium source, a supplemental bone formation agent parathyroid hormone (PTH) or its derivative (Kimmel et al., Endocrinology, 132: 1577-1584, 1993), PTHRP, a bone morphogenetic protein, osteogenin, NaF, $PGE_2$ agonists, a statin, and a RANK ligand (RANKL), including an osteogenic form of RANKL such as GST-RANKL or other oligomerized form of RANKL. At the end of the experiment, the animals are sacrificed and femurs, tibiae, and lumbar vertebrae1 to 4 are excised and collected. The proximal left and right tibiae are used for pQCT measurements, cancellous bone mineral density (BMD), and histology, while the mid-shaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed), LV3 are prepared for undecalcified bone histology, and LV4 are processed for mechanical testing.

In addition, osteoclast cultures, containing macrophages, osteoclast precursors and osteoclasts, can be generated from bone marrow precursors, as described herein, particularly from bone marrow macrophages and utilized in assessment of compounds for osteoclast modulating activity. Bone marrow macrophages are cultured in 48- or 96-well cell culture dishes in the presence of M-CSF (10-30 ng/ml), RANKL (30-100 ng/ml), with or without addition of compound(s) or control(s), and medium changed (e.g. on day 3). Osteoclast-like cells are characterized by staining for tartrate-resistant acid phosphatase (TRAP) activity. Bone resorption may be assessed for instance by using a pit assay, whereby osteoclasts may be generated on whale dentin slices from bone marrow macrophages. After three days of culture to generate osteoclasts, compound(s) or control(s) are added to the culture for two days. At the end of the experiment, cells are TRAP stained and photographed to document cell number. Cells are then removed from the dentin slices with 0.5M ammonium hydroxide and mechanical agitation. Maximum resorption lacunae depth is measured using a confocal microscope (Microradiance, Bio-Rad Laboratories, Hercules, Calif.). For evaluation of pit number and resorbed area, dentin slices are stained with Coomassie brilliant blue and analyzed with light microscopy using Osteomeasure software (Osteometrics, Decatur, Ga.) for quantitation.

In a preferred embodiment, osteoclast modulating ability of a compound is tested in an in vitro assay utilizing osteoclasts, osteoclast precursor cells or osteoclast-like cells. General protocols for treatment of osteoclasts with a compound are well established and known in the art. For instance, bone marrow macrophages may be utilized to generate osteoclasts in vitro as described herein. It is to be noted that the conditions used will vary according to the cell lines and compound used, their respective amounts, and additional factors such as plating conditions and media composition. Such adjustments are readily determined by one skilled in this art.

The function of osteoclasts or differentiation of osteoclast precursors may be determined by assessing the activation of intracellular proteins indicative of osteoclast differentiation and/or function, particularly including, but not limited to, proteins or kinases such as phospholipase Cγ1 (PLCγ), VAV, CBL, ERK and JNK, or proteins or kinases such as Rho and Rac. Thus, following the incubation of osteoclasts with a test compound, the cells are lysed and their intracellular contents subjected to the appropriate tests, such as Western blots, kinase assays, and electrophoretic mobility gel shift assays (EMSAs).

A Western blot can be generally performed as follows. Once the cell lysates are generated, the intracellular proteins are separated on the basis of size by utilizing SDS-PAGE (sodium dodecyl sulfate-polyacrylamide gel electrophoresis). The separated proteins are transferred by electroblotting to a suitable membrane (such as nitrocellulose or polyvinylidene flouride) to which they adhere. The membrane is washed to reduce non-specific signals, and then probed with an antibody which recognizes only the specific protein. After further washing, which removes excess antibody, a second antibody, which recognizes the first antibody and contains a reporter moiety is applied to the membrane. The addition of a developing agent, which interacts with a reporter moiety on the second antibody results in visualization of the bands.

An additional assay that can be applied to determine differentiation and/or function of osteoclasts is an electrophoretic mobility gel shift assay (EMSA). Briefly, an EMSA may be conducted as follows. Nuclei of treated osteoclasts are isolated and their extracts generated. The nuclear proteins are then incubated with a specific oligonucleotide probe that has been labeled $^{32}P$ orthophosphate. After an appropriate time, the putative protein-DNA complexes are separated on a PAGE gel (no SDS present), which is dried and exposed to an X-ray film. If a specific complex has formed, a band will be visible on the developed film. Typically, appropriate controls are run in parallel with the experimental sample(s) in order to ensure that the band is specific for activated osteoblasts. Detailed procedures on Western blotting and EMSA are described in Lai, et al. Lai, et al. (2001) J Biol Chem 276(17): 14443-14450). Additionally, cell-based assays for osteoclast differentiation and function, based on measuring or visualizing F-actin to detect the actin ring or by visualizing resorption pits by hematoxylin staining in bone marrow macrophage derived osteoclasts can be performed. In addition, proliferation of osteoclasts and osteoclast precursors in cultures of bone marrow macrophages may be assessed, e.g. by BrdU incorporation. These assays are well known in the art and easily performed by a skilled artisan.

In one embodiment, the method of screening osteoclast modulating compounds involves incubating a test compound with osteoclasts, osteoclast precursor cells or osteoclast-like cells under conditions sufficient for such incubation. The test compound may be a compound that binds an adenosine A1 receptor. Selecting the compounds that bind to the A1 receptor may be performed in multiple ways as described above and herein.

General protocols and assays for the treatment of osteoclasts with a compound are known to the skilled artisan and are described herein. Similarly, modulation of osteoclast differentiation and/or function may be performed as described above. The assays may consist of determining the activation of intracellular proteins correlated with osteoclast differentiation and/or function. These proteins include, but are not limited to phospholipase Cγ1 (PLCγ), VAV, CBL, ERK and JNK.

Candidate Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683).

Phage display libraries may be used to screen potential ligands or adenosine A1 receptor modulators. Their usefulness lies in the ability to screen, for example, a library displaying a billion different compounds with only a modest investment of time, money, and resources. For use of phage display libraries in a screening process, see, for instance, Kay et al., Methods, 240-246, 2001. An exemplary scheme for using phage display libraries to identify compounds that bind or interact with A1 receptor may be described as follows: initially, an aliquot of the library is introduced into microtiter plate wells that have previously been coated with target protein, e.g. A1 receptor. After incubation (e.g. 2 hrs), the non-binding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for the adenosine A1 receptor may be obtained by performing ELISAs. One skilled in the art can easily perform these experiments. In one aspect, an A1 receptor molecule used for any of the assays may be selected from a recombinant A1 receptor protein, or an A1 fusion protein, an analog, derivative, or mimic thereof.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

The methods of screening compounds may also include the specific identification or characterization of such compounds, whose osteoclast modulating potential was determined by the methods described above. If the identity of the compound is known from the start of the experiment, no additional assays are needed to determine its identity. However, if the screening for compounds that modulate the adenosine A1 receptor is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (see for instance neogenesis.com). Neogenesis' ALIS (automated ligand identification system) spectral search engine and data analysis software allow for a highly specific identification of a ligand structure based on the exact mass of the ligand. One skilled in the art can also readily perform mass spectrometry experiments to determine the identity of the compound.

Antibodies, including polyclonal and monoclonal antibodies, particularly anti-A1 receptor antibodies and neutralizing antibodies may be useful as compounds to modulate osteoclast differentiation and/or function. These antibodies are available from Upstate Biologicals, Santa Cruz, or they made be prepared using standard procedures for preparation of polyclonal or monoclonal antibodies known to those skilled in the art. Also, antibodies including both polyclonal and monoclonal antibodies, and drugs that modulate the activity of the adenosine A1 receptor and/or its subunits may possess certain diagnostic applications and may for example, be utilized for the purpose of detecting and/or measuring conditions such as bone diseases, bone loss, or osteoclast differentiation and/or function. The adenosine A1 receptor or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the A1 receptor may be discovered or synthesized, and may be used in diagnostic and/or therapeutic protocols.

Therapeutic and Prophylactic Compositions and Their Use

Candidates for therapy with the agents identified by the methods described herein are patients either suffering from a bone disease or bone condition characterized by bone loss or a decrease in bone mass or density, or are prone to development of such diseases. Subjects suffering from osteoporosis, juvenile osteoporosis, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases or malignancy-induced osteoporosis and bone lysis, childhood idiopathic bone loss, periodontal bone loss, age-related loss of bone mass, osteotomy and bone loss associated with prosthetic ingrowth, other forms of osteopenia are candidates for therapy with the compounds and agents of the present invention.

In addition, subjects suffering from other conditions where facilitation of bone repair or replacement is desired such as bone fractures, bone defects, plastic surgery, dental and other implantations are also candidates for therapy with the compounds and agents described herein.

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the agents identified by the methods described herein may be formulated as pharmaceutical compositions to be used for prophylaxis or therapeutic use to treat these patients.

Various delivery systems are known and can be used to administer a compound of the invention, e.g., encapsulation in liposomes, microparticles, or microcapsules. Methods of introduction can be enteral or parenteral and include but are not limited to intradernal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled or sustained release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

In a preferred embodiment of the invention, a method of preventing or inhibiting bone loss or of enhancing bone formation is provided by administering compositions comprising compounds that block or antagonize an adenosine receptor.

The present invention further contemplates therapeutic compositions useful in practicing the therapeutic methods of this invention. A subject therapeutic composition includes, in admixture, a pharmaceutically acceptable excipient (carrier) and one or more of an adenosine A1 receptor modulators, as described herein as an active ingredient. In a preferred embodiment, the composition comprises one or more compounds or agents capable of blocking or inhibiting the adenosine A1 receptor.

Effects of the compounds or agents of the invention can first be tested for their ability to block or inhibit the adenosine A1 receptor using standard techniques known in the art. More particularly, the selectivity of the compounds for the A1 receptor can be assessed using radioligand binding assays whereby a test or candidate compound can be assayed for its ability to compete for binding to a cell having or expressing the A1 receptor, or any of the other known adenosine receptors (A2A, A2B or A3). Cells can be transfected with the nucleic acid encoding the various adenosine receptors and competitive binding assays with radiolabeled ligands run to evaluate the specificity of the particular candidate compounds. The cDNAs for human $A_1$ (see GenBank accession number BC026340), A2A (see GenBank accession number NM_000675), A2B (see GenBank accession number NM_000676) or $A_3$ (see GenBank accession number AY136749 or L22607 or NM_000677) can be used to prepare the nucleic acid constructs for use in these methods.

Several adenosine A1 receptor antagonists have been identified to date. These are listed in Table 1 and can also be found in the following published U.S. patents and applications: U.S. Pat. Nos. 6,495,687; 6,489,332; 6,117,998; 6,605,601; 5,840,729; 5,786,360; 2005/0245546; 2005/0119258; 2005/0059683; 2005/0187226; 2003/0220358; 2003/0045536; 2002/0111333; and 2002/0082269, as well as in FIG. 2.

Osteoclast precursors or progenitor cells can be cultured as described herein and used to assess the effect of the adenosine A1 receptor antagonists on osteoclast cell differentiation, formation or function.

Further confirmation of the activity of the compounds can be tested in relevant in vivo models, for example, the osteoprotegerin-deficient mouse model described by Bucay et al. (Bucay, N. et al. (1998), Genes and development 12:1260-1268).

The present compounds or agents that modulate the adenosine A1 receptor, in particular, the antagonists or inhibitors of the A1 receptor, themselves can be used as the sole active agents, or can be used in combination with one or more other active ingredients. In particular, combination therapy using the adenosine A1 receptor antagonists with one or more other agents that have an effect in treating bone diseases or conditions characterized by bone loss or a decrease in bone mass or density are contemplated. These agents are known in the art, and can be selected from an antiresorptive drug, a bone-forming agent, an estrogen receptor antagonist and a drug that has a stimulatory effect on osteoclasts. More particularly, the antiresorptive drug may be selected a bisphosphonate, an estrogen or estrogen analogue, a selective estrogen receptor modulator (SERM) and a calcium source, Tibolone, calcitonin, a calcitriol and hormone replacement therapy. The bone-forming agent may be selected from parathyroid hormone (PTH) or a peptide fragment thereof, PTH-related protein (PTHrp), bone morphogenetic protein, osteogenin, NaF, a $PGE_2$ agonist, a statin, and a RANK ligand (RANKL). The drug that has a stimulatory effect on osteoclasts may be vitamin D, or a vitamin D derivative or mimic thereof. The estrogen receptor antagonist may be raloxifene, bazedoxifene and lasofoxifene. The bisphosphonate may be alendronate, risedronate, ibandronate and zoledronate. Compositions comprising one or more adenosine A1 modulators and one or more other antiresorptive or anabolic agents are provided and included in the invention.

When contemplating combination therapy with an adenosine A1 receptor antagonist and one or more of the above-noted agents, it is important to assess clinical safety by methods known to those skilled in the art. Appropriate dose titration may be necessary when certain groups of compounds are contemplated for use together.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the preferred embodiment, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). A hydrogel is defined as a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions, that have charged side groups, or a monovalent ionic salt thereof.

For use in treatment of animal subjects, the compositions of the invention can be formulated as pharmaceutical or veterinary compositions. Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The preparation of therapeutic compositions which contain small organic molecules polypeptides, analogs or active fragments as active ingredients is well understood in the art. The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, or intravenously. Formulations may be prepared in a manner suitable for systemic administration or for topical or local administration. Systemic formulations include, but are not limited to those designed for injection (e.g., intramuscular, intravenous or subcutaneous injection) or may be prepared for transdermal, transmucosal, nasal, or oral administration. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents which enhance the effectiveness of the active ingredient.

A small organic molecule/compound, a polypeptide, an analog or active fragment thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. For oral administration, the compositions can be administered also in liposomal compositions or as microemulsions. Suitable forms include syrups, capsules, tablets, as is understood in the art.

The compositions of the present invention may also be administered locally to sites in subjects, both human and other vertebrates, such as domestic animals, rodents and livestock, where bone formation and growth are desired using a variety of techniques known to those skilled in the art. For example, these may include sprays, lotions, gels or other vehicles such as alcohols, polyglycols, esters, oils and silicones. Such local applications include, for example, at a site of a bone fracture or defect to repair or replace damaged bone. Additionally, a bone modulating composition may be administered e.g., in a suitable carrier, at a junction of an autograft, allograft or prosthesis and native bone to assist in binding of the graft or prosthesis to the native bone.

The administration of the compositions of the present invention may be pharmacokinetically and pharmacodynamically controlled by calibrating various parameters of administration, including the frequency, dosage, duration mode and route of administration. Thus, in one embodiment bone mass formation is achieved by administering a bone forming composition in a non-continuous, intermittent manner, such as by daily injection and/or ingestion. Variations in the dosage, duration and mode of administration may also be manipulated to produce the activity required.

The therapeutic adenosine A1 receptor modulator (e.g. inhibitor) compositions are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the agent selected for treating the subject, the dosage formulation, and in a therapeutically effective amount. The phrase "in an amount sufficient to inhibit osteoclast differentiation, formation or function" refers to the amount of an adenosine receptor antagonist necessary to achieve localized (at the site of injury or diseased tissue or cells, e.g. bone or bone marrow) concentrations of the inhibitor. If one desires to achieve the desired effect in vitro, the effective amounts may range from about 0:1 nM to about 10 µM, more preferably about 0.1 nM to about 5 µM, and most preferably from about 0.1 nM to about 1 nM. The desired effect refers to the effect of the agent on osteoclast differentiation, formation or function, using the methods as described herein, and ultimately to an effect on amelioration of the symptoms associated with the bone disease or disorder, or a slowing of bone disease progression. Moreover, the quantity of the adenosine A1 receptor antagonist to be administered depends on the subject to be treated, and degree of inhibition of the adenosine A1 receptor desired or the extent or severity of bone disease. Precise amounts of active ingredient required to be administered depend on the judgment of the practitioner and are peculiar to each individual. However, suitable dosages to achieve the desired therapeutic effect in vivo may range from about 0.1 mg/kg body weight per day to about 200 mg/kg body weight per day, or from about 1.0 mg/kg body weight per day to about 100 mg/kg body weight per day, preferably about 25 mg/kg body weight per day to about 50 mg/kg body weight per day. In a particular embodiment, the term "about" means within 20%, preferably within 10%, and more preferably within 5%. The preferred dose will depend on the route of administration. However, dosage levels are highly dependent on the nature of the disease or situation, the condition of the subject, the judgment of the practitioner, and the frequency and mode of administration. If the oral route is employed, the absorption of the substance will be a factor effecting bioavailability. A low absorption will have the effect that in the gastro-intestinal tract higher concentrations, and thus higher dosages, will be necessary. Suitable regimes for initial administration and further administration are also variable, but are typified by an initial administration followed by repeated doses at one or more hour intervals by a subsequent injection or other administration. Alternatively, continuous intravenous infusion sufficient to maintain desired concentrations, e.g. in the blood, are contemplated. The composition may be administered as a single dose multiple doses or over an established period of time in an infusion.

It will be understood that the appropriate dosage of the substance should suitably be assessed by performing animal model tests, wherein the effective dose level (e.g. $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed.

The compound or composition of the present invention may be modified or formulated for administration at the site of bone or to bone cells, particularly osteoclasts. Such modification may include, for instance, formulation which facilitate or prolong the half-life of the compound or composition, particularly in the osteoclast environment. Additionally, such modification may include the formulation of a compound or composition to include a targeting protein or sequence which facilitates or enhances the uptake of the compound/composition to bone or bone precursor cells. In a particular embodiment, such modification results in the preferential targeting of the compound to bone or bone precursor cells versus other locations or cells. In one embodiment, a tetracycline, tetracycline family or bisphosphonate may be utilized to target the compound or composition of the present invention to bone or bone cells, including osteoclasts and osteoclast precursors. Novel heterocycles as bone targeting compounds are disclosed in U.S. Patent Publication No. 2002/0103161 A1, which is incorporated herein by reference in its entirety.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Effective Doses

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to unaffected cells and, thereby, reduce side effects.

The data obtained from cell culture assays and animal studies can be used in formulating a dose range for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to optimize efficacious doses for administration to humans. Plasma levels can be measured by any technique known in the art, for example, by high performance liquid chromatography.

In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Normal dose ranges used for particular therapeutic agents employed for specific diseases can be found in the *Physicians' Desk Reference* 54th Edition (2000).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of Adenosine a1 Receptor on Osteoclast Formation and osteoclastic bone resorption Materials and Methods Media and Reagents Recombinant Mouse RANKL, recombinant mouse M-CSF, DPCPX and N6-CPA were purchased from Sigma. Lymphocyte separation medium was purchased from Fisher. α-MEM (Cambrex Bio Science Rockland, Inc, USA) was used for all incubations supplemented with 10% heat-inactivated FBS, 2 mM L-glutamine, 100 IU/ml penicillin, and 100 μg/ml streptomycin (all from Sigma-Aldrich). All cultures were maintained at 37° C. in a humidified atmosphere of 5% $CO_2$ in air.

Animals

Mice with a targeted disruption of the gene for the A1 adenosine receptor have been described in detail elsewhere (Johansson, B. et al. (2001), Proc. Natl. Acad. Sci. USA, 98:9407-9412; Gimenez-Llort, L. et al. (2002), Eur. J. Neurosci. 16:547-550). Mice were housed in the New York University (NYU) animal facility, fed regular mouse chow, and given access to drinking water ad libitum. The experiments reported here were performed on female mice. All procedures described below were reviewed and approved by the Institutional Animal Care and Use Committee of NYU Medical Center and carried out under the supervision of the facility veterinary staff.

In Vitro Osteoclast Formation Assays

Isolation and Culture of Bone Marrow Precursors

Bone marrow cells were isolated from 5- to 8-wk-old C57BL/6 female mice. Femurs and tibiae were aseptically removed and dissected free of adherent soft tissues. The bone ends were cut, and the marrow cavity was flushed out with medium αMEM from one end of the bone using a sterile 21-gauge needle. The bone marrow suspension was carefully agitated with a plastic Pasteur pipette to obtain a single-cell suspension. The cells were washed twice and resuspended ($3.75 \times 10^5$ cells/ml) in α MEM containing 10% FBS, and this suspension was added to 24-well plates (500 μl/well). To each of these wells an additional 500 μl of medium containing M-CSF (30 ng/ml) and RANKL (30 ng/ml) without or with various concentrations of DPCPX and N6-CPA were added. Cultures were fed every 3 days by replacing 500 μl of culture medium with an equal quantity of fresh medium and reagents. After incubation for 7 days, wells were prepared for tartrate-resistant acid phosphatase (TRAP) staining. The number of TRAP-positive multinucleated cells (MNCs) containing three or more nuclei was scored.

Isolation and Culture of Spleen Cells

Spleen cells were isolated from 5- to 8-wk-old C57BL/6 female mice as previously described (Cronstein, et al J. Clinl. Invest. 92:2675, 1993) with modification. In brief, spleens were placed on top of a 100 μm cell strainer in 50 ml falcon, mashed with a plunger and the released cells were rinsed through the strainer with 8 ml PBS. The nonadherent cells were layered on top of the lymphocyte separation medium. The cells were centrifuged at 1500 rpm for 20 minutes. The macrophage/lymphocyte white band was located about 1 cm below the top of the LSM. The PBS was aspirated until 1 ml above the band, then 1 ml was removed to a 50 ml Falcon tube including the band. To this Falcon tube was added 19 ml PBS and the tube was then centrifuged at 1500 rpm for 15 minutes.

PBS was removed and 10 ml aMEM was added and the cells were counted under a light microscope. The cells were resuspended ($3.75 \times 10^5$ cells/ml) in αMEM containing 10% FBS, and this suspension was added to 24-well plates (500 µl/well) as described above.

Characterization of Osteoclasts

Osteoclast formation was evaluated by quantification of Tartrate-Resistant Acid Phosphatase (TRAP)-positive multinucleated cells (MNCs) using a modification of the method of Burstone. (Burstone MS 1958 Histochemical demonstration of acid phosphatases with naphthol AS-phosphate. J Natl Cancer Inst 21:423-539) with modification. TRAP is preferentially expressed at high levels in osteoclasts and is considered, especially in the mouse, to be an osteoclast marker. After incubation, cells on wells were washed in PBS, fixed in 4% paraformaldehyde for 10 min, and stained for acid phosphatase in the presence of 0.3 M sodium tartrate (Sigma-Aldrich). The substrate used was napthol AS-BI phosphate (Sigma-Aldrich). Only those cells that were strongly TRAP-positive (dark red) and have more than 3 nuclei were counted by light microscopy.

RNA Isolation and RT-PCR

Osteoclasts as described above were prepared in 24 well plates. Expression of TRAP, RANK, RANKL, OPG, DC-STAMP, and GAPDH mRNAs was assessed by RT-PCR. RNA was isolated using the TRIzol reagent (Sigma) and used for cDNA synthesis. The cDNA was amplified using PCR for 35 cycles. Each cycle consisted of 30 s of denaturation at 94° C. and 30 s of annealing and 30 s of extension at 72° C. The sequences of primers used were TRAP-mF, 5'-GGAT-TCATGGGTGGTGCTG-3' (SEQ. I.D. NO: 1); TRAP-mR, 5'-TGGCTAACAATGGTCGCAAG-3' (SEQ. I.D. NO: 2); RANKL-mF, CCA GCA TCA AAA TCC CAA GTT (SEQ. I.D. NO: 3); RANKL-mR, TCA AGG TTC TCA GTG GCA CAT (SEQ. I.D. NO: 4); RANK-mf, CCA TCA TCT TCG GCG TTT ACT (SEQ. I.D. NO: 5); RANK-mR, ACT GTC GTT CTC CCC CAC TT (SEQ. I.D. NO: 6); OPG-mf, 5'-TG-GCACACAGTGATGAATGCG-'3 (SEQ. I.D. NO: 7); OPG-mR, 5'-GCTGGAAAGTTTGCTCTTGCG-3' (SEQ. I.D. NO: 8); mDC-STAMP forward primer 5'-TTGCCGCTGTG-GACTATCTG-3' (SEQ. I.D. NO: 9); mDC-STAMP reverse primer 5'-GAATGCAGCTCGGTTCAAAC-3' (SEQ. I.D. NO: 10).

Results

DPCPX Inhibits Osteoclastogenesis by Acting on Osteoclast Precursors

Figure 1:
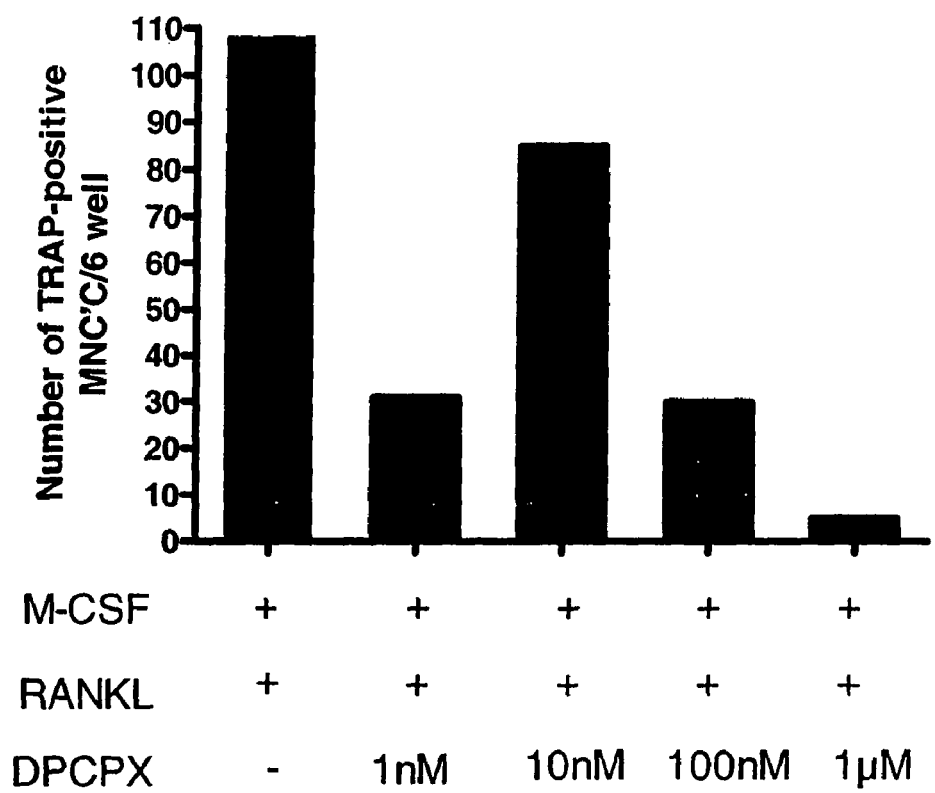
FIG. 1. Effect of DPCPX on osteoclast formation by bone marrow cells. Bone marrow cells of 6- to 8-wk-old CD57/b16 female mice were incubated in 24-well plates ($3 \times 10^5$ cells/well) in the presence of M-CSF and RANKL (30 ng/ml of each) in the absence or the presence of increasing concentrations of DPCPX. After 7 days cells were fixed and stained for TRAP, and the number of TRAP-positive MNCs per well was scored. (Similar results were obtained in three independent experiments).

To investigate the role of DPCPX on osteoclast differentiation, we first examined the effect of DPCPX on RANKL-induced osteoclast formation from bone marrow cells. To generate osteoclasts, bone marrow cells were incubated for 7 days with M-CSF (30 ng/ml) and RANKL (30 ng/ml). In these cultures RANKL induced the formation of a large number of mononuclear and multinuclear (more than three nuclei) TRAP-positive cells in the presence of M-CSF. These TRAP-positive cells displayed features of bona fide osteoclasts, including the capacity to resorb bone (data not shown). Increasing concentrations of recombinant mouse DPCPX were added to the culture of bone marrow cells on day 0 with M-CSF and RANKL. DPCPX strikingly inhibited the number of TRAP-positive cells in a dose-dependent manner (FIG. 1). A DPCPX concentration of 1 nM was sufficient to significantly inhibit osteoclast formation, while complete inhibition was seen at 1 µM. In the absence of RANKL, no TRAP-positive cells were seen in cultures incubated with M-CSF and DPCPX (data not shown).

Figure 2:
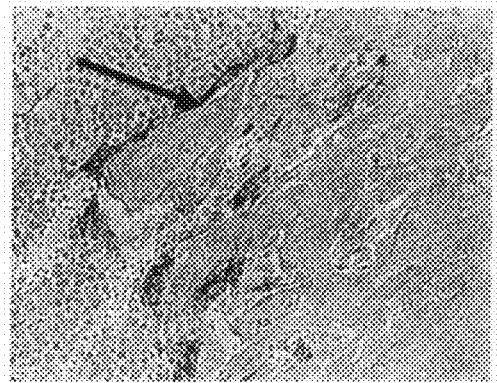
FIG. 2. Osteoclast Formation in Adenosine A1 Receptor Deficient Mice in Response to RANKL and MCSF. 6-Week old adenosine A1 knockout and wild type littermate mice were sacrificed, bones decalcified and fixed and stained for tartrate resistant alkaline phosphatase, a marker for osteoclasts (Arrow). As shown in the panel on the left, multinucleated osteoclasts in wild type mice adhere tightly to bone and leave scalloped resorption pits. On the right, the osteoclasts of the $A_1$ receptor knockout mice are not adherent to the bone nor are normal resorption areas noted.
Figure 2:
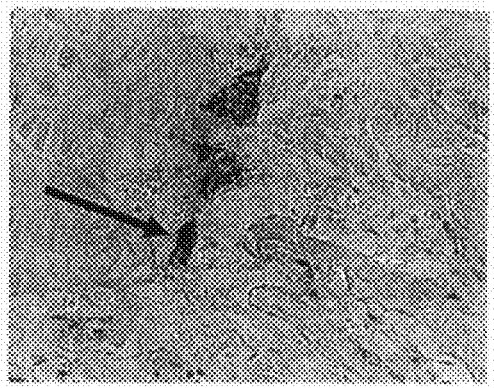

To confirm that the effects of the A1 adenosine receptor-selective antagonist were mediated via blockade of adenosine A1 receptors we determined the capacity of macrophages from adenosine A1 receptor deficient mice to form osteoclasts in response to RANKL and M-CSF. We found a significantly decreased number of osteoclasts formed from the cells of A1 receptor knockout mice (120±24 vs. 21±3, N=5, P=0.003). When studied in vivo there were fewer multinucleated osteoclasts in A1 knockout mice and what osteoclasts there were neither attached to bone nor resorbed it normally (FIG. 2).

Because there appeared to be a defect in osteoclast formation in the A1 receptor knockout mice, we examined the long bones of mice and found that in the A1 knockout mice there were fewer, if any, osteoclasts and that the bony spicules were significantly thicker, consistent with osteopetrosis.

Example 2

Additional Studies on the Effect of Adenosine Receptor Antagonists on Osteoclastogenesis and on Bone Loss Due to Ovariectomy Materials and Methods Media and Reagents Recombinant Mouse RANKL, recombinant mouse M-CSF, DPCPX were purchased from Sigma. Lymphocyte separation medium was purchased from Fisher. α-MEM (Cambrex Bio Science Rockland, Inc, USA) was used for all incubations supplemented with 10% heat-inactivated FBS, 2 mM L-glutamine, 100 IU/ml penicillin, and 100 µg/ml streptomycin (all from Sigma-Aldrich). All cultures were maintained at 37° C. in a humidified atmosphere of 5% $CO_2$ in air. Anti-P65, anti-$I_\kappa B_\alpha$, anti-NFATc1, anti-foc, anti-TRAF6, anti-JNK1, anti-p38, anti-phospho-JNK1/2, anti-phospho p38 and anti-phospho-ERK1/2 antibodies were purchased from Santa Cruz Biotechnology (Santa Cruz, Calif.).

Animals

Mice with a targeted disruption of the gene for the A1 adenosine receptor have been described in detail elsewhere (Johansson, B. et al. (2001), Proc. Natl. Acad. Sci. USA, 98:9407-9412; Gimenez-Liort, L. et al. (2002), Eur. J. Neurosci. 16:547-550). Mice were housed in the New York University (NYU) animal facility, fed regular mouse chow, and given access to drinking water ad libitum. The experiments reported here were performed on Female mice. All procedures described below were reviewed and approved by the Institutional Animal Care and Use Committee of NYU Medical Center and carried out under the supervision of the facility veterinary staff.

Isolation and Culture of Splenocytes

Splenocytes were isolated from 5- to 8-wk-old C57BL/6 female mice aspreviously described with modification. In brief, spleens were putted on top of 100 µm cell strainer in 50 ml falcon, mashed with plunger and rinsed the released cells through the strainer with 8 ml PBS. The nonadherent cells were layered on top of the lymphocyte separation medium. The cells were spin 1500 rpm for 20 minutes. The macrophages/lymphocyte white band was located about 1 cm below the top of the LSM. The PBS was aspirated until 1 ml above the band then 1 ml was removing to 50 ml Falcon including the band. To this Falcon 19 ml PBS was added and spine 1500 rpm for 15 minutes. PBS was removed and 10 ml αMEM was added. The cells were resuspended ($3 \times 10^5$ cells/ml) in αMEM containing 10% FBS, and this suspension was added to 24-well plates (50011/well) as described above.

Characterization of Osteoclasts

Osteoclast formation was evaluated as described above, that is, by quantification of TRAP-positive MNCs as described previously (Burstone MS 1958 Histochemical demonstration of acid phosphatases with naphthol AS-phosphate. J Natl Cancer Inst 21:423-539). TRAP is preferentially expressed at high levels in osteoclasts and is considered, especially in the mouse, to be an osteoclast marker. After incubation, cells on wells were washed in PBS, fixed in 4% paraformaldehyde for 10 min, and stained for acid phosphatase in the presence of 0.3 M sodium tartrate (Sigma-Aldrich). The substrate used was napthol AS-BI phosphate (Sigma-Aldrich). Only those cells that were strongly TRAP-positive (dark red) and have more than 3 nuclei were counted by light microscopy.

Histology

Mouse Tibia were excised, cleaned of soft tissue, and decalcified in EDTA. Histologic sections were stained with hematoxylin and eosin, van kossa, cathepsin K or for tartrate-resistant acid phosphatase (TRAP) activity.

Electron Microscopy of Osteoclasts

Both tibiae from five animals were fixed in 2.5% glutaraldehyde in 0.1 M sodium cacodylate buffer (pH 7.4) for 12 hours at ambient temperature. After being rinsed three times for 20 min in the same buffer, the material was post fixed for 6 hours in 1% osmium tetroxide (in 0.1 M sodium cacodylate buffer), dehydrated in acetone and embedded. Sections were prepared, stained with Cathepsin K and examined in the electron microscope. The thin sections were scanned systematically and all osteoclasts encountered were photographed.

Western Blotting

Osteoclast precursors were preincubated with M-CSF (30 ng/ml) with or without DPCPX (10 ng/ml) for 3 days and stimulated with RANKL (30 ng/ml) for the indicated period. For isolation of total proteins, cells were washed twice with PBS and lysed in buffer containing 50 mM Tris (pH 7.5), 150 mM NaCl, 1% Nonidet P40, 1% Triton X-100, 1% sodium deoxycholate, 0.1% SDS, 50 mM NaF, 1 mM $Na_3VO_4$, 20 mM sodium glycerophosphate, 1 mM EDTA, 2 mM PMSF, 1 mM benzamidine, and 1× protease inhibitor cocktail (Sigma-Aldrich). For isolation of cytoplasmic and nuclear proteins, cells were washed twice with PBS and lysed in hypotonic buffer containing 10 mM HEPES (pH 7.5), 10 mM KCl, 3 mM NaCl, 3 mM $MgCl_2$, 1 mM EDTA, 1 mM EGTA, and 2 mM DTT with protease and phosphatase inhibitors as mentioned above. After 20-min incubation on ice, 0.05 vol of 10% Nonidet P-40 was added, and the cells were vortexed and immediately centrifuged at 500×g for 10 min at 4° C. The supernatants were collected as cytoplasmic extract. The pelleted nuclei were suspended in 50 μl of ice-cold nuclear buffer containing 20 mM HEPES (pH 7.5), 25% glycerol, 0.8 M KCl, 1 mM $MgCl_2$, 1% Nonidet P-40, 0.5 mM EDTA, 2 mM DTT, and protease and phosphatase inhibitors as mentioned above. The samples were incubated on ice for 30 min (with occasional mixing) and then centrifuged (14,000×g for 15 min at 4° C.). The supernatants were collected as nuclear extracts. Proteins were estimated. Sixty micrograms of proteins boiled with sample buffer (0.125 M Tris (pH 6.8), 4% SDS, 20% glycerol, 2% 2-ME, and 0.03 mM bromophenol blue) for 5 min were subjected to electrophoresis on 10% SDS-PAGE. Proteins were transferred onto a nitrocellulose membrane. Membranes were blocked overnight in blocking solution (5% nonfat dry milk in TBS containing 0.1% Tween 20) and exposed to primary Abs for 1 h at room temperature. After washing, the membranes were incubated for 1 h at room temperature with HRP-labeled secondary Ab, and the labeled proteins were detected using ECL reagents according to the manufacturer's instructions. To reprobe the membranes with other Abs, the membranes were stripped with 100 mM 2-ME, 2% SDS, and 62.5 mM Tris-HCl (pH 6.9) for 20 min at 50° C., followed by immunoblotting as described above.

Total RNA Extraction/RT-PCR from Splenocytes

After the cultured cells became confluent in tissue culture flasks and were passaged three times, the cell suspensions were lysed in Trizol reagent (Invitrogen Life Technologies, UK), and total RNA from dissolved specimens was extracted according to the manufacturer's instructions. First, single stranded complementary DNA (cDNA) was synthesized from total RNA from each sample using a cDNA synthesis kit (Invitrogen Life Technologies, UK). cDNA was then amplified by polymerase chain reaction (PCR) to generate products corresponding to mRNA encoding mice gene products for c-Fos, PU.1 and GAPDH mRNAs was assessed by RT-PCR. The sequences of primers used were c-Fos, sense 5'-GGA GGA CCT TAC CTG TTC GTGA-3' (SEQ. I.D. NO: 21); c-Fos antisense 5'-GAACAACACACTCCATGCGG-3' (SEQ. I.D. NO: 22); PU.1.- sense 5'-ATGTGCTTCCCTTAT-CAAACCT-3' (SEQ. I.D. NO: 23); PU.1 antisense 5'-CTTGTGCTTGGACGAGAACTG-3' (SEQ. I.D. NO: 24); mDC-STAMP forward primer 5'- TTGCCGCTGTGGAC-TATCTG-3' (SEQ. I.D. NO: 9); mDC-STAMP reverse primer 5'- GAATGCAGCTCGGTTCAAAC-3' (SEQ. I.D. NO: 10).

Ovariectomy

6 Week old C57bl/6 female mice received ovariectomy or a sham procedure in which the ovaries were exteriorized but not removed. Mice were sacrificed 5 weeks after the surgical procedure. Mice were treated with either water alone or DPCPX dissolved in water and adjusted, based on the weight of the animals, to a dose of 50 mg/kg/d.

Bone Density Measurements

In vivo bone density measurements in 12 $A_1$WT and 7 $A_1$KO were performed by dual energy x-ray absorptiometry, using a PIXImus densitometer (Lunar Corp., Madison, Wis.). Measurements were made at 6 months of age. Anesthetized mice (30 mg ketamine/kg body wt and 3 mg xylazine/kg body wt, ip) were placed in the prone position and scans were performed and an acquisition time of 5 min. Bone mineral content (BMC) is expressed as gram and Bone Mineral Density (BMD) is expressed as milligrams per centimeter squared. The coefficient of variation for total body BMD is approximately 0.34%.

Micro-X-Ray Computed Tomography (μCT) Analysis of Bone

Femoral μCT was measured as described (Hildebrand T, Rüegsegger P. A new method for the model-independent assessment of thickness in three-dimensional images. J Microsc 1997; 185:67-75) by using a MS-8 (MS-8, GE Healthcare, London, Ontario, Canada) at 18 μm isotropic resolution-scans calibrated by air, water and a mineral standard material phantom/Parker algorithm for digital reconstruction.

Results

Figure 4:
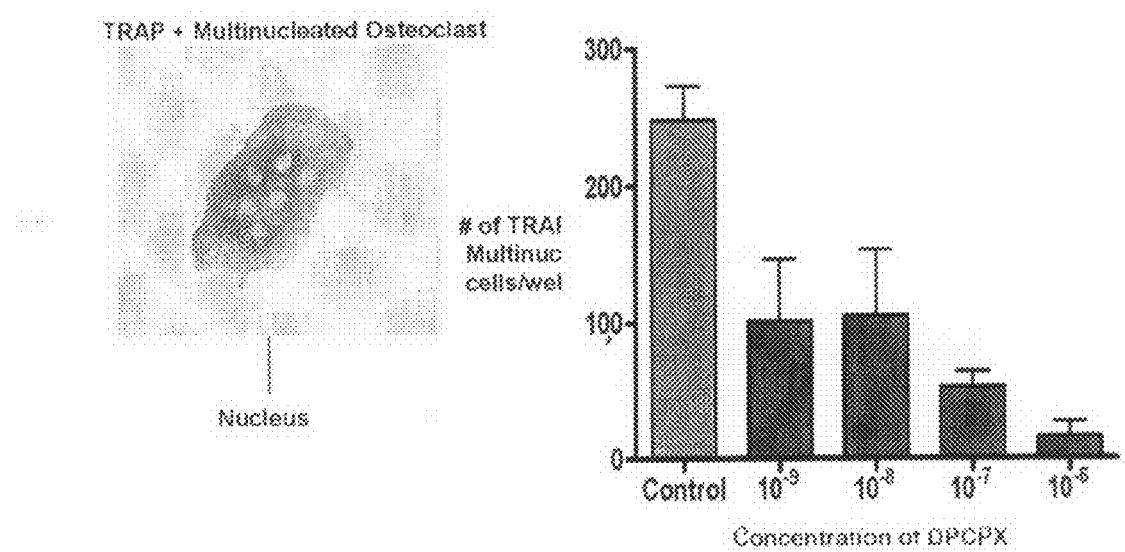
FIG. 4. Effect of DPCPX on osteoclast formation by Splenocytes. Splenocytes of 6-to 8-wk-old CD57/b16 female mice were incubated in 24-well plates ($3 \times 10^5$ cells/well) in the presence of M-CSF and RANKL (30 ng/ml) in the absence or the presence of increasing concentrations of DPCPX. After 7 days cells were fixed and stained for TRAP, and the number of TRAP-positive MNCs per well was scored. (Similar results were obtained in three independent experiments).

The Adenosine $A_1$ Receptor Antagonist DPCPX Inhibits Osteoclastogenesis by Splenocytes To investigate the role of adenosine $A_1$ receptors in osteoclast differentiation, we first examined the effect of DPCPX on RANKL-induced osteoclast formation by murine splenocytes. To generate osteoclasts splenocytes were incubated for 7 days with M-CSF (30 ng/ml) and RANKL (30 ng/ml). In these cultures RANKL induced the formation of a large number of mononuclear and multinuclear (more than three nuclei) TRAP-positive cells in the presence of M-CSF. Increasing concentrations of DPCPX were added to the culture of splenocytes on day 0 with M-CSF and RANKL. DPCPX strikingly diminished the number of TRAP-positive multinucleated cells in a dose-dependent manner (FIG. 4). A DPCPX concentration of 1 nM significantly inhibited osteoclast formation, while almost complete inhibition was seen at 1 µM. In the absence of RANKL, no TRAP-positive cells were seen in cultures incubated with M-CSF and DPCPX (data not shown).

DPCPX Inhibits Osteoclastogenesis by Acting on Osteoclast Precursors

Figure 5:
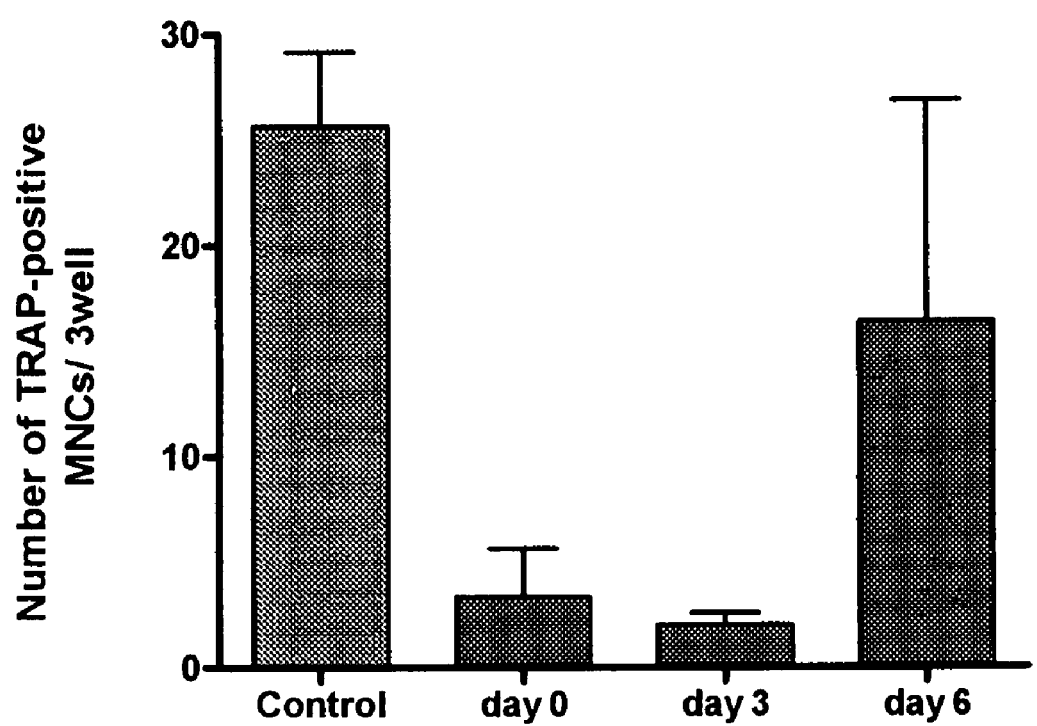
FIG. 5. DPCPX Inhibits Osteoclastogenesis by Acting on Osteoclast Precursors. Osteoclast precursors were cultured in the presence of M-CSF and RANKL, and DPCPX was added to the culture on days 0, 3, and 6. After culture for 7 days with DPCPX, cells were stained for TRAP. Results are expressed as the mean±SEM of three cultures per variable.

To determine at which stage DPCPX inhibits osteoclast differentiation, osteoclast precursors were incubated with M-CSF, RANKL and DPCPX was added on day 0, 3 and 6. After culture for a total of 7 days with DPCPX, TRAP-positive multinucleated cells were enumerated. DPCPX inhibited osteoclast formation when added on day 0, and inhibition decreased when DPCPX addition was delayed (FIG. 5). These results suggest that DPCPX primarily targets early osteoclast precursors.

Diminished Osteoclast Formation by Splenocytes from $A_1$ Receptor Knockout Mice To confirm that the effects of the A1 adenosine receptor-selective antagonist were mediated via blockade of adenosine A1 receptors, we determined the capacity of splenocytes from adenosine $A_1$ receptor deficient mice to form osteoclasts in response to RANKL and M-CSF. We found that no osteoclasts formed from the cells of $A_1$ receptor knockout mice (FIG. 6). These results clearly confirm the hypothesis that adenosine $A_1$ receptors play a critical role in osteoclastogenesis in vitro. Because there appeared to be a defect in osteoclast formation in the $A_1$ receptor knockout mice, we examined the long bones of mice and found that in the $A_1$ knockout mice there were fewer osteoclasts.

Effect of $A_1$ Receptor Blockade (DPCPX) on PU.1 and c-Fos mRNA Expression

Next, the effect of the A1 receptor antagonist DPCPX (1 µM) and CPA (1 µM) on other critical transcription factors for osteoclast formation, such as PU.1 and c-Fos, was examined (FIG. 7). PU.1 is a myeloid-specific transcription factor, and PU.1 knockout mice were found to be osteopetrotic due to the arrest in the development of both osteoclasts and macrophages. c-Fos is a component of the dimeric transcription factor AP-1. Disruption of the proto-oncogene c-fos gives rise to severe osteopetrotic disorders in bone caused by a defect in osteoclast progenitors. In this study DPCPX (1 µM) does not affect PU.1 or c-Fos mRNA expression indicating that $A_1$ receptor blockade modulates osteoclast formation by affecting a downstream element in osteoclast formation.

$A_1$ Receptor Blockade Prevents RANKL-Induced Nuclear Translocation of NF-κB by Inhibiting Degradation of IκB To further investigate the mechanism of action of DPCPX, the effect of DPCPX on distal components of RANK signaling was examined. Distal events in RANK signaling include activation of the NF-κB complex via TRAF6. Since RANKL is a strong inducer of NFκB and plays a key role in osteoclast differentiation, the effect of DPCPX on RANKL-induced degradation of IκB was examined. Osteoclast precursors were incubated for 3 days in the presence of M-CSF and RANKL with or without DPCPX. Cells were lysed, fractionated by SDS-PAGE, and analyzed by Western blotting. As shown in FIG. 8, DPCPX treatment for 3 days inhibited RANKL-induced degradation of IκB. Next, to examine the effect of DPCPX on RANKL-induced nuclear translocation of NF-κB, osteoclast precursors were incubated for 3 days in the presence of M-CSF and RANKL with or without DPCPX. Cells were lysed, and cytoplasmic and nuclear fractions were separated. Cytosols were examined for IκBα, p50, and p65 NF-κB, and nuclear extracts were examined for p50 and p65 NF-κB by immunoblots. The data in FIG. 8 show that RANKL induces nuclear translocation of p50 and p65 subunits, decreases the cytoplasmic levels of these two proteins, and also induces degradation of IκB. Consistent with DPCPX inhibition of phosphorylation and degradation of IκB, DPCPX when added, totally prevents the nuclear translocation of p50 and p65 and causes these proteins to accumulate in the cytoplasm and prevent the degradation of IκB. In other studies we have found that when adenosine $A_1$ receptors are blocked by DPCPX, TRAF6, a critical intermediate mediator of NFκB activation, is lost from the cell. This phenomenon has previously been described as resulting from ubiquitination and proteasomal degradation of the protein (Data not Shown).

Skeletal Phenotype of a Denosine $A_1$ Receptor Knockout Mice

Based on the demonstration that adenosine A1 receptors play a critical role in osteoclast formation and function, we asked whether animals lacking $A_1$ receptors had increased bone mineral density as compared to wild type control mice. Histologic sections of bones from $A_1$ Knockout mice and their wild type littermate controls showed increased bone density (FIG. 9A). Staining of bone sections for osteoclasts (immunohistology for Cathepsin K) revealed that there was no decrease in the number of osteoclasts in the $A_1$ knockout mice but the osteoclasts in these mice appeared smaller and were often not associated with bone (FIG. 9B). Electron microscopic examination of the osteoclasts in these mice further demonstrated that the osteoclasts in the knockout mice did not have ruffled borders and did not appear to be resorbing bone (FIG. 10). Consistent with these results we found that $A_1$ knockout mice had significantly increased bone mineral density (BMD) when compared with wild-type littermates (FIG. 11 and Table 2). The $A_1$KO mice and their normal littermates had no differences in external appearance or bodyweight. There were no abnormalities in tooth eruption, as has been seen in other forms of osteopetrosis and the relative size and shape of the bones in the $A_1$KO mice were not different from those of control mice although their mineralization was markedly increased. Thus, these studies clearly indicate that adenosine A1 receptors play a critical role in osteoclast maturation and function and loss of the receptor leads to an increase in bone density, osteopetrosis.

Effects of $A_1$R Antagonist Treatment (DPCPX) on Bone Loss due to Ovariectomy

Because we observed that the adenosine $A_1$ receptor plays a critical role in the formation and function of osteoclasts, we reasoned that an agent that blocks adenosine $A_1$ receptors might prevent pathologic bone loss. The most common form of osteoporosis in the United States is post-menopausal osteoporosis when, following the loss of hormonal stimulation due to menopause, bone loss is accelerated. We determined whether adenosine $A_1$ receptor antagonist treatment of mice following ovariectomy could block bone loss and treated these animals for 5 weeks with DPCPX in their water (50 mg/kg/d). As shown in FIG. 12, the $A_1$ antagonist treated mice did not lose bone mass following ovariectomy, as shown by microCT study. These studies clearly demonstrate that adenosine $A_1$ receptor blockade prevents bone loss due to surgical menopause and suggests the utility of adenosine $A_1$ receptor antagonists in the treatment of pathologic bone loss due to menopause as well as the many other causes of pathologic bone loss (e.g. associated with glucocorticoid treatment).

Example 3

Measurement of Adenosine A1 Receptor Affinity

Methods

A1 Receptor Affinity

The test described below may be used to determine the potency of test compounds to compete with the ligand $^3$H-cyclohexyladenosine for the adenosine A1 receptor prepared from rat brain membranes.

Animals

Male Sprague-Dawley rats are sacrificed by decapitation and the membranes are isolated from whole animal brains. (See R. Goodman, et al., Guanine Nucleotide and Cation Regulation of the Binding of $^3$H-Diethylphenylxanthine to Adenosine A1 Receptors in Brain Membrane, Molecular Pharmacology, 21, 329-335 (1982)).

Preparation of Membranes

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 µl of $^3$H-cyclohexyladenosine, 0.8 nM in the assay, 200 µl of test compounds at various concentrations over the range of $10^{-10}$ M to $10^{-6}$ M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omniflour containing 5% Protosol.

Specific binding of $^3$H-cyclohexyladenosine is measured as the excess over blanks taken in the presence of $10^{-5}$ M 2-chloroadenosine. Total membrane-bound radioactivity is about 5% of that added to the test tubes. Specific binding to membranes is about 90% of the total bound. Protein content of the membrane suspension is determined by the method of O. H. Lowry, et al., Protein Measurements With Folin Phenol Reagent, J. Biol. Chem., 193, 265-275 (1951).

Displacement of $^3$H-cyclohexyladenosine binding of 15% or more by a test compound is indicative of affinity for the adenosine binding site.

Example 4

Other Adenosine Receptor Binding Assays

Stable Transfection of HEK-293 or CHO Cells

The cDNAs for human A1 (see GenBank accession number BC026340 and SEQ. I.D. NOs: 11 and 12), A2A (see GenBank accession number NM_000675 and SEQ. I.D. NOs: 13 and 14), A2B (see GenBank accession number NM_000676 and SEQ. I.D. NOs: 15 and 16) or A3 (see GenBank accession number AY136749 (NM020683) SEQ. I.D. NOs: 17 and 18 or L22607 SEQ. I.D. NOs: 19 and 20) adenosine receptors (AdoRs) are prepared by RT-PCR from total RNA of human cells or tissues and sequenced on both strands. The expression vector containing each of these cDNAs and a second vector containing a neomycin or puromycin-resistance gene are introduced to HEK-293 or CHO cells by Lipofectin-Plus (Life Technology). Colonies are selected by growing transfected cells in the presence of neomycin or puromycin. Stably transfected cells are maintained in Dulbecco's modified Eagle's medium (DMEM) or F-12 medium with 10% fetal bovine serum, 100 µg/ml penicillin, 100 µg/ml streptomycin and appropriate concentrations of neomycin or puromycin. These stably transfected cells are referred to as HEK-"AdoR" or CHO-"AdoR" depending on the receptors that they express. The cell lines used routinely are CHO-A1, HEK-A2A, HEK-A2B and CHO-A3 cells. In addition, hamster DDT1 MF-2 cells that express endogenous A1 AdoRs are also used to determine the binding activities of compounds for A1 AdoRs Membrane Preparation Monolayers of transfected cells or DDT1 MF-2 are washed with phosphate buffered saline (PBS) and harvested in a buffer containing 10 mM HEPES (pH 7.4), 10 mM EDTA and protease inhibitors. The cells are homogenized in polytron for 1 minute at setting 4 and centrifuged at 29000 g for 15 minutes at 4° C. The cell pellets are washed with a buffer containing 10 mM HEPES (pH7.4), 1 mM EDTA and protease inhibitors, and are resuspended in the same buffer supplemented with 10% sucrose. Frozen aliquots are kept at −80° C.

Radioligand Binding

The affinities of compounds for A1, A2A, A2B or A3 AdoRs are determined in competition studies using radioligands such as $^3$H-CPX (A1 antagonist), or $^3$H-CCPA (A1 agonist), $^3$H-ZM241385 (A2A antagonist) or $^3$H-CGS21680 (A2A agonist), $^3$H-ZM241385 (A2B antagonist) or $^{125}$I-AB-MECA (A3 agonist) and membranes of corresponding cells. For example, to determine the affinity for A1 AdoRs, the competition assays are started by mixing 0.5-1 nM $^3$H-CPX with various concentrations of test compounds and 25-100 µg membrane proteins of CHO-$A_1$ or DDT1 MF-2 in TE buffer (50 mM Tris and 1 mM EDTA) supplemented with 1 U/ml adenosine deaminase. The assays are incubated for 60-90 minutes, stopped by filtration onto GF/B filter plates using Packard Harvester and washed four times with ice-cold TM buffer (10 mM Tris, 1 mM MgCl2, pH 7.4). The amounts of radioligands that bind to the GF/B filter plates are determined by scintillation counting. Nonspecific binding is determined in the presence of 1-10 µM of cold ligands. $B_{max}$ and $K_D$ values are calculated using GraphPad software.

cAMP Measurements

Cells are harvested using 0.0025% trypsin and 2 mM EDTA in PBS, washed and resuspended in phenol-free DMEM to a concentration of $1 \times 10^6$ cells/ml, and then incubated with 1 U/ml of adenosine deaminase for 30 minutes at room temperature. Cells are then treated with various agonists, antagonists and/or forskolin in the presence or absence of 50 µM phosphodiesterase IV inhibitor, rolipram. After incubating for 5-30 minutes at 37° C., cells are lysed and cAMP concentrations are determined using cAMP-Screen Direct™ System (Applied Biosystem) according to the manufacturer's instructions.

Example 5

Effect of A1 Receptor on Osteoclast Formation: Osteoclast Formation Assay

Using an osteoclast formation assay, treatment with an A1 receptor antagonist may be shown to inhibit osteoclast formation and activity in ovariectomized mice, as described previously. Briefly, bone marrow cells are isolated from ovariectomized mice by flushing mouse femurs with 5 ml α-MEM. The marrow cells are cultured as noted previously for 7 days in α-MEM containing 10% FCS, 30 ng/ml of M-CSF and 30 ng/ml of RANKL and are then stained for osteoclasts by detecting tartrate-resistant acid phosphastase (TRAP) activity. Osteoclasts are quantitated using light microscopy.

Example 6—Assessment of Candidate Compounds

Potential candidate or test compounds can be assessed using any of the above-noted materials and methods or any of the following materials and methods.

Materials and Methods

Adenosine deaminase and HEPES are purchased from Sigma (St. Louis, Mo.). Ham's F-12 cell culture medium and fetal bovine serum are purchased from GIBCO Life Technologies (Gaithersburg, Md.). Antibiotic G-418, Falcon 150 mM culture plates and Costar 12-well culture plates are purchased from Fisher (Pittsburgh, Pa.). [3H]CPX is purchased from DuPont-New England Nuclear Research Products (Boston, Mass.). Penicillin/streptomycin antibiotic mixture is purchased from Mediatech (Washington, D.C.). The composition of HEPES-buffered Hank's solution is: 130 mM NaCl, 5.0 mM Cl, 1.5 mM CaCl2, 0.41 mM MgSO.4, 0.49 mM Na.2HPO.4, 0.44 mM KH.2PO.4, 5.6 m dextrose, and 5 mM HEPES (pH 7.4).

Membrane Preparation

Rat A1 Receptor: Membranes are prepared from rat cerebral cortex isolated from freshly euthanized rats. Tissues are homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 min. Pellets are resuspended and washed twice with buffer HE (10 mM Na-HEPES, 1 mM EDTA, pH 7.4, plus protease inhibitors). Final pellets are resuspended in buffer HE, supplemented with 10% (w/v) sucrose and protease inhibitors, and frozen in aliquots at −80° C. Protein concentrations are measured using BCA protein assay kit (Pierce).

Human A1 Receptor: Human A1 adenosine receptor (A1AR) cDNA is obtained by RT-PCR and subcloned into pcDNA3.1 (Invitrogen). Stable transfection of CHO-K1 cells is performed using LIPOFECTAMINE-PLUS (GIBCO-BRL) and colonies are selected in 1 mg/ml G418, and screened using radioligand binding assays. For membrane preparations, CHO-K1 cells growing as monolayers in complete media (F12+10% FCS+1 mg/ml G418) are washed in PBS and harvested in buffer A supplemented with protease inhibitors. Cells are homogenized, centrifuged, and washed twice with buffer HE as described above. Final pellets are stored in aliquots at −80 degree C.

Radioligand Binding Assays

Membranes (50 μg membrane protein for rat A1ARs, and 25 μg of CHO-K1 membrane protein for human A1ARs), radioligands and varying concentrations of competing ligands are incubated in triplicates in 0.1 ml buffer HE plus 2 units/ml adenosine deaminase for 2.5 h at 21° C. Radioligand [3H]DPCPX (112 Ci/mmol from NEN, final concentration: 1 nM) is used for competition binding assays on A1 ARs. Non-specific binding is measured in the presence of 10 μM BG9719. Binding assays are terminated by filtration over Whatman GF/C glass fiber filters using a BRANDEL cell harvester. Filters are rinsed three times with 3-4 ml ice-cold 10 mM Tris-HCl, pH 7.4 and 5 mM MgCl 2 at 4° C. Filter paper is transferred to a vial, and 3 ml of scintillation cocktail ScintiVerseII (Fisher) is added. Radioactivity is counted in a Wallac β-counter.

Analysis of Binding Data

For K1 Determinations: Competition binding data are fit to a single-site binding model and plotted using Prizm Graph-Pad. Cheng-Prusoff equation K1=IC50/(1+[I]/KD) is used to calculate KI values from IC50 values, where KI is the affinity constant for the competing ligand, [I] is the concentration of the free radioligand, and KD is the affinity constant for the radioligand.

For % Binding: For one-point binding assays, data is presented as % of total specific binding at 1 μM of competing compound: % of total=100* (Specific binding with 1 μM of competing compound/total specific binding). % binding represents the amount of bound radioligand remaining in the presence of 1 μM of competing antagonist.

CHO cells stably expressing the recombinant human A1AdoR (CHO:A1AdoR cells) are prepared as described (Kollias-Barker et al., J. Pharma. Exp. Ther. 281(2), 761, 1997) and cultured as for CHO:Wild cells. CHO cells are cultured as monolayers on plastic dishes in Ham's F-12 medium supplemented with 10% fetal bovine serum, 100 U penicillin G and 100 μg streptomycin in a humidified atmosphere of 5% CO2/95% air at 37° C. The density of [3H]CPX binding sites in CHO cells is 26+-2 (n=4) fmol/mg protein. Cells are subcultured twice weekly after detachment using 1 mM EDTA in Ca2+-Mg2+-free HEPES-buffered Hank's solution. Three different clones of CHO:A1AdoR cells are used for experiments, and all results are confirmed with cells from two or three clones. The density of A1AdoRs in these cells is 4000-8000 fmol/mg protein, as determined by assay of [3H]CPX specific binding.

Radioligand Binding

CHO cells grown on 150 mm culture dishes are rinsed with HEPES-buffered Hank's solution, then removed with a cell scraper and homogenized in ice-cold 50 mM Tris-HCl, pH 7.4. Cell membranes are pelleted by centrifugation of the cell homogenate at 48,000×g for 15 minutes. The membrane pellet is washed twice by resuspension in fresh buffer and centrifugation. The final pellet is resuspended in a small volume of 50 mM Tris-HCl, pH 7.4, and stored in aliquots of 1 ml at −80° C. until used for assays.

To determine the density of A1AdoRs in CHO cell membranes, 100 μl aliquots of membranes (5 μg protein) are incubated for 2 hours at 25° C. with 0.15-20 nM [3H]CPX and adenosine deaminase (2 U/ml) in 100 μl of 50 mM Tris-HCl, pH 7.4. Incubations are terminated by dilution with 4 ml of ice-cold 50 mM Tris-HCl buffer and immediate collection of membranes onto glass-fiber filters (Schleicher and Schuell, Keene, N. H.) by vacuum filtration (Brandel, Gaithersburg, Md.). Filters are washed quickly three times with ice-cold buffer to remove unbound radioligand. Filter discs containing trapped membranes bound radioligand are placed in 4 ml of Scintiverse BD (Fisher), and the radioactivity is quantified using a liquid scintillation counter. To determine nonspecific binding of [3H]CPX, membranes are incubated as described above and 10 μM CPT is added to the incubation buffer. Nonspecific binding is defined as [3H]CPX bound in the presence of 10 μM CPT. Specific binding of the radioligand to the A1AdoR is determined by subtracting nonspecific binding from total binding. Nonspecific binding is found to increase linearly with an increase of [3H]CPX concentration. Triplicate assays are done at each tested concentration of [3H]CPX.

To determine the affinities of antagonists of A1AdoRs for the human recombinant A1 AdoRs expressed in CHO cells, binding of 2 nM [3H]CPX in the presence of increasing concentrations of antagonist is measured. Aliquots of CHO cell membranes (100 μl: 5 μg protein), [3H]CPX, antagonist (0.1 nM-100 μM), and adenosine deaminase (2 U/ml) are incubated for 3 hours at 25° C. in 200 μl of 50 mM Tris-HCl buffer (pH 7.4). Assays are terminated as described above.

TABLE 1

ADENOSINE A1 RECEPTOR ANTAGONISTS (XANTHINE AND NON-XANTHINE ANTAGONISTS)

| DESIGNATION | CHEMICAL NAME |
|---|---|
| DPCPX | 8-cyclopentyl-1,3-dipropylxanthine |
| CPT (C-102) | 8-cyclopentyl-1,3-dimethylxanthine |
| N-0840 (N-154) | $N^6$-cyclopentyl-9-methyladenine |
| WRC-0571 | C8-(N-Methylisopropyl)amino-$N^6$-(5'-endohydroxy-endonorbornan)-2-yl-9- methyladenine |
| N-0861 | ($N^6$-endonorbornan-2yl-9-methyladenine |
| WRC-0342 | [$N^6$-($5^1$-endohydroxy)-endonorbornan-2-yl-9-methyladenine |
| CGS-15943 | 9-chloro-2-(2-furanyl)[1,2,4]triazole[1,5-C]-quinazolin-5 amine |
| DPCPX | 1,3-dipropyl-8-cyclopentylxanthine |
| XAC | Xanthine amine congener |
| KW-3902 | 8-(noradamantan-3-yl)-1,3-dipropyl xanthine |
| ENX | 1,3-dipropyl-8-[-2-(5,6-epoxynorbornyl)]xanthine |
| BIIP20 (KFM19) | ((S)-(-)-8-(3-oxocyclopentyl)-1,3-dipropyl-1H-purine-2,6-dione) |
| FK453 | (R)-1-[(E)-3-(2-phenulpyrazolo[1,5a]pyridin-3-yl)acryloyl]-2-piperidine ethanol |
| FK352 | (R)-1-[(E)-3-(2-phenulpyrazolo[1,5-a]pyridin-3-yl)-acryloyl]-piperidin-2-yl acetic acid. |
| FK838 | 6-oxo-3-(2-phenylpyrazolo[1,5-a]pyridine-3-yl)-1(6H-pyridazine butyric acid) |
| BG9719 (aka CVT-124) | The S-enantiomer of 1,3-dipropyl-8-[2-(5,6-epoxynorbornyl]xanthine |
| BG9928 | (3-[4-(2,6-dioxo-1,3-dipropyl-2,3,6,7-tetrahydro-1H-purin-8-yl)-bicyclo[2-.2.2]oct-1-yl]-proprionic acid |
| FR166124 | A 3-(2-cycloalkyl or cycloalkenyl-3-oxo-2,3-dihydropyridazin-6-yl)-2-phenylpyrazo lo [1,5-a]-pyridine analog |

TABLE 2

COMPARISON OF SKELETAL PHENOTYPE FROM WILD TYPE AND $A_1$ RECEPTOR KNOCKOUT MICE

|  | $A_1$WT |  | $A_1$KO |  | t-test |
|---|---|---|---|---|---|
| Bone Volume/Tissue Volume BV/TV | 7.6 ± 0.9 | N = 4 | 12.5 ± 1.4 | N = 4 | 0.01 |
| Trabecular number (Tb. N.) | 2.0 ± 0.13 | N = 4 | 3.1 ± 0.24 | N = 4 | 0.003 |
| Trabecular thickness (Tb. Th.) | 2.2 ± 0.14 | N = 4 | 2.6 ± 0.13 | N = 4 | 0.04 |
| Trabecular seperation (Tb. Sep.) | 0.5 ± 0.03 | N = 4 | 0.3 ± 0.03 | N = 4 | 0.003 |
| Cortical Thicknesses | 0.5 ± 0.03 | N = 4 | 0.6 ± 0.02 | N = 4 | 0.01 |

What is claimed is:

1. A method for inhibiting osteoclast differentiation, formation, or function in a patient in need thereof, comprising administering to said patient an agent that blocks or antagonizes the adenosine A1 receptor, in an amount sufficient to inhibit osteoclast differentiation, formation or function, wherein the agent is a small organic molecule.

2. The method of claim 1, wherein the adenosine A1 receptor antagonist is CVT-124.

3. The method of claim 1, wherein the adenosine A1 receptor antagonist is administered orally or parenterally.

4. The method of claim 1, wherein the adenosine A1 receptor antagonist is administered intravenously, subcutaneously, intramuscularly, or intravasally.

5. The method of claim 1, wherein the adenosine A1 receptor antagonist is administered via an implanted device.

6. The method of claim 5, wherein the implanted device is an osmotic pump.

7. The method of claim 1, wherein the adenosine A1 receptor antagonist is administered in combination with a therapeutically effective amount of one or more other compounds or agents effective for treating a bone disease or condition characterized by loss of bone or a decrease in bone mass.

8. The method of claim 7, wherein the one or more other compounds or agents effective for treating a bone disease or condition is selected from the group consisting of an antiresorptive drug, a bone-forming agent, an estrogen receptor antagonist and a drug that has a stimulatory effect on osteoblasts.

9. The method of claim 8, wherein the antiresorptive drug is selected from the group consisting of a bisphosphonate, an estrogen or estrogen analogue, a selective estrogen receptor modulator (SERM) and a calcium source, Tibolone, calcitonin, and a calcitriol.

10. The method of claim 8, wherein the bone-forming agent is parathyroid hormone (PTH) or a peptide fragment thereof, PTH-related protein (PTHrp), a bone morphogenetic protein, osteogenin, NaF, a $PGE_2$ agonist, a statin, and a RANK ligand (RANKL).

11. The method of claim 10, wherein the PTH peptide fragment is teriparatide.

12. The method of claim 8, wherein the drug that has a stimulatory effect on osteoblasts is vitamin D, or a vitamin D derivative.

13. The method of claim 8, wherein the estrogen receptor antagonist is selected from the group consisting of raloxifene, bazedoxifene and lasofoxifene.

14. The method of claim 9, wherein the bisphosphonate is selected from the group consisting of alendronate, risedronate, ibandronate and zoledronate.

15. A method of increasing bone mass or ameliorating loss of bone mass in a subject suffering from a condition characterized by low bone mass, the method comprising administering to said subject a therapeutically effective amount of an adenosine A1 receptor antagonist, wherein the A1 receptor antagonist is a small organic molecule.

16. The method of claim 15, wherein the condition is selected from the group consisting of osteoporosis, juvenile osteoporosis, bone loss due to/ or associated with the onset of menopause, osteoporotic fractures, giant cell tumors of bone, renal osteodystrophy, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, malignancy-induced osteoporosis and bone lysis, periodontal bone loss, age-related loss of bone mass, osteotomy and bone loss associated with prosthetic ingrowth, and other forms of osteopenia.

17. The method of claim 15, wherein the adenosine A1 receptor antagonist is CVT-124.

18. The method of claim 15, wherein the adenosine A1 receptor antagonist is administered orally or parenterally.

19. The method of claim 15, wherein the adenosine A1 receptor antagonist is administered intravenously, subcutaneously, intramuscularly, or intravasally.

20. The method of claim 15, wherein the adenosine A1 receptor antagonist is administered via an implanted device.

21. The method of claim 20, wherein the implanted device is an osmotic pump.

22. The method of claim 15, wherein the adenosine A1 receptor antagonist is administered in combination with a therapeutically effective amount of one or more other compounds or agents effective for treating a bone disease or condition characterized by loss of bone or a decrease in bone mass.

23. The method of claim 22, wherein the one or more other compounds or agents effective for treating a bone disease or condition is selected from the group consisting of an antiresorptive drug, a bone-forming agent, an estrogen receptor antagonist and a drug that has a stimulatory effect on osteoblasts.

24. The method of claim 23, wherein the antiresorptive drug is selected from the group consisting of a bisphosphonate, an estrogen or estrogen analogue, a selective estrogen receptor modulator (SERM) and a calcium source, Tibolone, calcitonin, a calcitriol and hormone replacement therapy.

25. The method of claim 23, wherein the bone-forming agent is parathyroid hormone (PTH) or a peptide fragment thereof, PTH-related protein (PTHrp), a bone morphogenetic protein, osteogenin, NaF, a $PGE_2$ agonist, a statin, and a RANK ligand (RANKL).

26. The method of claim 25, wherein the PTH peptide fragment is teriparatide.

27. The method of claim 23, wherein the drug that has a stimulatory effect on osteoblasts is vitamin D, or a vitamin D derivative.

28. The method of claim 23, wherein the estrogen receptor antagonist is selected from the group consisting of raloxifene, bazedoxifene and lasofoxifene.

29. The method of claim 24, wherein the bisphosphonate is alendronate, risedronate, ibandronate and zoledronate.

* * * * *

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
ggattcatgg gtggtgctg                                                    19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tggctaacaa tggtcgcaag                                                   20

```
<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ccagcatcaa atcccaagt t                                                  21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
tcaaggttct cagtggcaca t                                                 21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ccatcatctt cggcgtttac t                                                 21

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
actgtcgttc tcccccactt                                                   20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tggcacacag tgatgaatgc g                                                 21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gctggaaagt ttgctcttgc g                                                 21

<210> SEQ ID NO 9
<211> LENGTH: 20
<212> TYPE: DNA
<213> ORGANISM: Artificial Sequence
<220> FEATURE:
<223> OTHER INFORMATION: primer
```

<400> SEQUENCE: 9
ttgccgctgt ggactatctg                                        20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gaatgcagct cggttcaaac                                        20

<210> SEQ ID NO 11
<211> LENGTH: 2756
<212> TYPE: DNA
<213> ORGANISM: Homo sapiens

<400> SEQUENCE: 11

```
agttcctgcg ccgggggcga cagagccgca ggcgcccgag tcgagtccca gccagctacc    60
atccctctgg agcttaccgg ccggccttgg cttccccagg aatccctgga gctagcggct   120
gctgaaggcg tcgaggtgtg ggggcacttg gacagaacag tcaggcagcc gggagctctg   180
ccagctttgg tgaccttggg tgcttgcctc gtgcccttg gtgcccgtct gctgatgtgc    240
ccagcctgtg cccgccatgc cgccctccat ctcagctttc caggccgcct acatcggcat   300
cgaggtgctc atcgccctgg tctctgtgcc cgggaacgtg ctggtgatct gggcggtgaa   360
ggtgaaccag cgcgctgcggg attccaccct ctgcttcatc gtgccgctgg cggtggctga   420
tgtggccgtg ggtgccctgg tcatcccct cgccatcctc atcaacattg ggccacagac   480
ctacttccac acctgcctca tggttgcctg tccggtcctc atcctcaccc agagctccat   540
cctggccctc tggcaattg ctgtggacca ctacctccgg gtcaagatcc ctctccggta   600
caagatggtg gtgacccccc ggagggcggc ggtggccata gccggctgct ggatcctctc   660
cttcgtggtg ggactgaccc ctatgtttgg ctggaacaat ctgagtgcgg tggagcgggc   720
ctgggcagcc aacggcagca tggggagcc cgtgatcaag tgcgagttcg agaaggtcat   780
cagcatggag tacatggtct acttcaactt ctttgtgtgg gtgctgcccc cgcttctcct   840
catggtcctc atctacctgg aggtcttcta cctaatccgc aagcagctca acaagaaggt   900
gtcggcctcc tccggcgacc cgcagaagta ctatgggaag gagctgaaga tcgccaagtc   960
gctggccctc atcctcttcc tctttgccct cagctggctg cctttgcaca tcctcaactg  1020
catcaccctt ttctgccagt cctgccacaa gcccagcatc cttacctaca ttgccatctt  1080
cctcacgcac ggcaactcgg ccatgaaccc cattgtctat gccttccgca tccagaagtt  1140
ccgcgtcacc ttccttaaga tttggaatga ccatttccgc tgccagcctg cacctcccat  1200
tgacgaggat ctcccagaag agaggcctga tgactagacc ccgccttccg ctcccaccag  1260
cccacatcca gtggggtctc agtccagtcc tcacatgccc gctgtcccag ggtctccct   1320
gagcctgccc cagctgggct gttggctggg gcatggggg aggctctgaa gagatacca   1380
cagagtgtgg tccctccact aggagttaac taccctacac ctctgggccc tgcaggaggc  1440
ctgggagggc aagggtccta cggagggacc aggtgtctag aggcaacagt gttctgagcc  1500
cccacctgcc tgaccatccc atgagcagtc cagcgcttca gggctgggca ggtcctgggg  1560
aggctgagac tgcagaggag ccatctgggc tgggagaagg tgcttgggct tctgcggtga  1620
```

-continued

```
ggcagggggag tctgcttgtc ttagatgttg gtggtgcagc cccaggacca agcttaagga    1680
gaggagagca tctgctctga gacggatgga aggagagagg ttgaggatgc actggcctgt    1740
tctgtaggag agactggcca gaggcagcta aggggcagga atcaaggagc ctccgttccc    1800
acctctgagg actctggacc ccaggccata ccaggtgcta gggtgcctgc tctccttgcc    1860
ctgggccagc ccaggattgt acgtgggaga ggcagaaagg gtaggttcag taatcatttc    1920
tgatatttgc tggagtgctg gctccacgca ctggggagtg agcttggtgc ggtaggtgct    1980
ggcctcaaac agccacgagg tggtagctct gagccctcct tcttgccctg agctttccgg    2040
ggaggagcct ggagtgtaat tacctgtcat ctgggccacc agctccactg gcctgcccgt    2100
tgccgggcct ggactgtcct aggtgacccc atctctgctg cttctgggcc tgatggagag    2160
gagaacacta gacatgccaa ctcgggagca ttctgcctgc ctgggaacgg ggtggacgag    2220
ggagtgtctg taaggactca gtgttgactg taggcgcccc tggggtgggt ttagcaggct    2280
gcagcaggca gaggagagta ccccctgag agcatgtggg ggaaggcctt gctgtcatgt    2340
gaatccctca atacccctag tatctggctg ggttttcagg ggctttggaa gctctgttgc    2400
aggtgtccgg gggtctagga ctttagggat ctggggaagg accaacccat gccctgccaa    2460
gcgtggagcc cctgtgttgg ggggcaaggt gggggagcct ggagcccctg tgtgggaggg    2520
cgaggcgggg gagcctggag cccctgtgtg ggagggcgag gcgggggatc ctggagcccc    2580
tgtgtcgggg ggcgagggag gggaggtggc cgtcgagttg accttctgaa catgagtgtc    2640
aactccagga cttgcttcca agcccttccc tctgttggaa attgggtgtg ccctggctcc    2700
caagggaggc ccatgtgact aataaaaaac tgtgaacccg aaaaaaaaaa aaaaaa       2756
```

<210> SEQ ID NO 12
<211> LENGTH: 326
<212> TYPE: PRT
<213> ORGANISM: Homo sapiens

<400> SEQUENCE: 12

```
Met Pro Pro Ser Ile Ser Ala Phe Gln Ala Ala Tyr Ile Gly Ile Glu
 1               5                  10                  15

Val Leu Ile Ala Leu Val Ser Val Pro Gly Asn Val Leu Val Ile Trp
            20                  25                  30

Ala Val Lys Val Asn Gln Ala Leu Arg Asp Ser Thr Phe Cys Phe Ile
        35                  40                  45

Val Pro Leu Ala Val Ala Asp Val Ala Val Gly Ala Leu Val Ile Pro
    50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp His Tyr Leu Arg Val Lys Ile Pro
            100                 105                 110

Leu Arg Tyr Lys Met Val Val Thr Pro Arg Arg Ala Val Ala Ile
        115                 120                 125

Ala Gly Cys Trp Ile Leu Ser Phe Val Val Gly Leu Thr Pro Met Phe
    130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175
```

```
Met Glu Tyr Met Val Tyr Phe Asn Phe Phe Val Trp Val Leu Pro Pro
            180                 185                 190
Leu Leu Leu Met Val Leu Ile Tyr Leu Glu Val Phe Tyr Leu Ile Arg
        195                 200                 205
Lys Gln Leu Asn Lys Lys Val Ser Ala Ser Ser Gly Asp Pro Gln Lys
    210                 215                 220
Tyr Tyr Gly Lys Glu Leu Lys Ile Ala Lys Ser Leu Ala Leu Ile Leu
225                 230                 235                 240
Phe Leu Phe Ala Leu Ser Trp Leu Pro Leu His Ile Leu Asn Cys Ile
                245                 250                 255
Thr Leu Phe Cys Gln Ser Cys His Lys Pro Ser Ile Leu Thr Tyr Ile
            260                 265                 270
Ala Ile Phe Leu Thr His Gly Asn Ser Ala Met Asn Pro Ile Val Tyr
        275                 280                 285
Ala Phe Arg Ile Gln Lys Phe Arg Val Thr Phe Leu Lys Ile Trp Asn
    290                 295                 300
Asp His Phe Arg Cys Gln Pro Ala Pro Pro Ile Asp Glu Asp Leu Pro
305                 310                 315                 320
Glu Glu Arg Pro Asp Asp
                325

<210> SEQ ID NO 13
<211> LENGTH: 2403
<212> TYPE: DNA
<213> ORGANISM: Homo sapiens

<400> SEQUENCE: 13
tttgcaggtg cctcaggaac cctgaagctg ggctgagcca tgatgctgct gccagaaccc      60
ctgcagaggg cctggtttca ggagactcag agtcctctgt gaaaaagccc ttggagagcg     120
ccccagcagg gctgcacttg ctcctgtga ggaaggggct caggggtctg gcccctccg      180 cctgggccgg gctgggagcc aggcgggcgg ctgggctgca gcaatggacc gtgagctggc     240
ccagcccgcg tccgtgctga gcctgcctgt cgtctgtggc catgcccatc atgggctcct     300
cggtgtacat cacggtggag ctggccattg ctgtgctggc catcctgggc aatgtgctgg     360
tgtgctgggc cgtgtggctc aacagcaacc tgcagaacgt caccaactac tttgtggtgt     420
cactggcggc ggccgacatc gcagtgggtg tgctcgccat ccccttttgcc atcaccatca     480 gcaccgggtt ctgcgctgcc tgccacggct gcctcttcat tgcctgcttc gtcctggtcc     540
tcacgcagag ctccatcttc agtctcctgg ccatcgccat tgaccgctac attgccatcc     600
gcatcccgct ccggtacaat ggcttggtga ccggcacgag ggctaagggc atcattgcca     660
tctgctgggt gctgtcgttt gccatcggcc tgactcccat gctaggttgg aacaactgcg     720
gtcagccaaa ggagggcaag aaccactccc agggctgcgg ggagggccaa gtggcctgtc     780
tctttgagga tgtggtcccc atgaactaca tggtgtactt caacttcttt gcctgtgtgc     840 tggtgccct gctgctcatg ctgggtgtct atttgcggat cttcctggcg gcgcgacgac     900
agctgaagca gatggagagc cagcctctgc cgggggagcg ggcacggtcc acactgcaga     960
aggaggtcca tgctgccaag tcactggcca tcattgtggg gctctttgcc ctctgctggc    1020 tgccctaca catcatcaac tgcttcactt tcttctgccc cgactgcagc cacgcccctc    1080
tctggctcat gtacctggcc atcgtcctct cccacaccaa ttcggttgtg aatcccttca    1140
tctacgccta ccgtatccgc gagttccgcc agaccttccg caagatcatt cgcagccacg    1200
tcctgaggca gcaagaacct ttcaaggcag ctggcaccag tgcccgggtc ttggcagctc    1260
```

```
atggcagtga cggagagcag gtcagcctcc gtctcaacgg ccacccgcca ggagtgtggg    1320
ccaacggcag tgctccccac cctgagcgga ggcccaatgg ctatgccctg ggctggtga    1380 gtggaggag tgcccaagag tcccagggga acacgggcct cccagacgtg agctcctta     1440 gccatgagct caagggagtg tgcccagagc ccctggcct agatgacccc ctggcccagg    1500
atggagcagg agtgtcctga tgattcatgg agtttgcccc ttcctaaggg aaggagatct    1560
ttatctttct ggttggcttg accagtcacg ttgggagaag agagagagtg ccaggagacc    1620
ctgagggcag ccggttccta ctttggactg agagaaggga gccccaggct ggagcagcat    1680
gaggcccagc aagaagggct tgggttctga ggaagcagat gtttcatgct gtgaggcctt    1740
gcaccaggtg ggggccacag caccagcagc atctttgctg gcaggccca gccctccact     1800 gcagaagcat ctggaagcac caccttgtct ccacagagca gcttgggcac agcagactgg    1860
cctggccctg agactgggga gtggctccaa tagcctcctg ccacccacac accactctcc    1920
ctagactctc ctagggttca ggagctgctg ggcccagagg tgacatttga cttttttcca    1980
ggaaaaatgt aagtgtgagg aaacccttttt tatttttatta cctttcactc tctggctgct    2040
gggtctgccg tcggtcctgc tgctaacctg gcaccagagc ctctgcccgg ggagcctcag    2100
gcagtcctct cctgctgtca cagctgccat ccacttctca gtcccagggc catctcttgg    2160
agtgacaaag ctgggatcaa ggataggag ttgtaacaga gcagtgccag agcatgggcc    2220
caggtcccag gggagaggtt ggggctggca ggccactggc atgtgctgag tagcgcagag    2280
ctacccagtg agaggccttg tctaactgcc tttccttcta aagggaatgt ttttttctga    2340
gataaaataa aaacgagcca catcgtgttt taagcttgtc caaatgaaaa aaaaaaaaa    2400 aaa                                                                 2403

<210> SEQ ID NO 14
<211> LENGTH: 412
<212> TYPE: PRT
<213> ORGANISM: Homo sapiens

<400> SEQUENCE: 14

Met Pro Ile Met Gly Ser Ser Val Tyr Ile Thr Val Glu Leu Ala Ile
  1               5                  10                  15

Ala Val Leu Ala Ile Leu Gly Asn Val Leu Val Cys Trp Ala Val Trp
             20                  25                  30

Leu Asn Ser Asn Leu Gln Asn Val Thr Asn Tyr Phe Val Val Ser Leu
         35                  40                  45

Ala Ala Ala Asp Ile Ala Val Gly Val Leu Ala Ile Pro Phe Ala Ile
     50                  55                  60

Thr Ile Ser Thr Gly Phe Cys Ala Ala Cys His Gly Cys Leu Phe Ile
 65                  70                  75                  80

Ala Cys Phe Val Leu Val Leu Thr Gln Ser Ser Ile Phe Ser Leu Leu
                 85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160
```

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
    370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410

<210> SEQ ID NO 15
<211> LENGTH: 1885
<212> TYPE: DNA
<213> ORGANISM: Homo sapiens

<400> SEQUENCE: 15
gggcaatttg ttagttatcc gccgccacca agacgcggca cggcgcctgg accggagggg      60
ccccgcgcgg gcgcgaactt tgggctcggg cgagtgggtg gtgctccgcc cagcccgaga     120
cgggcgggcg cgcgggccaa tggtgccgc ctcttggccg cggggggccc cgacccgtgg      180
gtcccggcca ccagcgcccc agccccgagg ctcagaagcg gcaggcggag gcgcggtccg     240
ggcgctatgg ccatgcccgg cgggtctcac gcggctgccc ctcgcccggc gcgccttcgg     300 taggggcgc ccggggccca gctggcccgg ccatgctgct ggagacacag gacgcgctgt      360
acgtggcgct ggagctggtc atcgccgcgc tttcggtggc gggcaacgtg ctggtgtgcg     420
ccgcggtggg cacggcgaac actctgcaga cgcccaccaa ctacttcctg gtgtccctgg     480
ctgcggccga cgtggccgtg gggctcttcg ccatcccctt tgccatcacc atcagcctgg     540
gcttctgcac tgacttctac ggctgcctct tcctcgcctg cttcgtgctg gtgctcacgc     600
agagctccat cttcagcctt ctggccgtgg cagtcgacag ataccggcc atctgtgtcc      660 cgctcaggta taaaagtttg gtcacgggga cccgagcaag agggtcatt gctgtcctct      720

```
gggtccttgc ctttggcatc ggattgactc cattcctggg gtggaacagt aaagacagtg    780
ccaccaacaa ctgcacagaa ccctgggatg gaaccacgaa tgaaagctgc tgccttgtga    840
agtgtctctt tgagaatgtg gtccccatga gctacatggt atatttcaat ttctttgggt    900
gtgttctgcc cccactgctt ataatgctgg tgatctacat taagatcttc ctggtggcct    960
gcaggcagct tcagcgcact gagctgatgg accactcgag gaccaccctc cagcgggaga   1020
tccatgcagc caagtcactg ccatgattg tggggatttt tgccctgtgc tggttacctg     1080
tgcatgctgt taactgtgtc actcttttcc agccagctca gggtaaaaat aagcccaagt    1140
gggcaatgaa tatggccatt cttctgtcac atgccaattc agttgtcaat cccattgtct    1200
atgcttaccg gaaccgagac ttccgctaca cttttcacaa aattatctcc aggtatcttc    1260
tctgccaagc agatgtcaag agtgggaatg gtcaggctgg ggtacagcct gctctcggtg    1320
tgggcctatg atctaggctc tcgcctcttc caggagaaga tacaaatcca caagaaacaa    1380
agaggacacg gctggttttc attgtgaaag atagctacac ctcacaagga aatggactgc    1440
ctctcttgag cacttccctg gagctaccac gtatctagct aatatgtatg tgtcagtagt    1500
aggctccaag gattgacaaa tatatttatg atctattcag ctgcttttac tgtgtggatt    1560
atgccaacag cttgaatgga ttctaacaga ctcttttgtt tttaaaagtc tgccttgttt    1620
atggtggaaa attactgaaa ctattttact gtgaaacagt gtgaactatt ataatgcaaa    1680
tactttttaa cttagaggca atggaaaaat aaaagttgac tgtactaaaa atgtatactt    1740
gttgccagga aggtgacctc aaaaattaaa agtataatta ttcggccggg catggtggct    1800
cacacctgta attccagcac tttgggaggc caaggcaggc ggatcacgag gtcaggagtt    1860
caaaaccagc ctgtccaata tagtg                                         1885

<210> SEQ ID NO 16
<211> LENGTH: 332
<212> TYPE: PRT
<213> ORGANISM: Homo sapiens

<400> SEQUENCE: 16

Met Leu Leu Glu Thr Gln Asp Ala Leu Tyr Val Ala Leu Glu Leu Val
 1               5                  10                  15

Ile Ala Ala Leu Ser Val Ala Gly Asn Val Leu Val Cys Ala Ala Val
                20                  25                  30

Gly Thr Ala Asn Thr Leu Gln Thr Pro Thr Asn Tyr Phe Leu Val Ser
             35                  40                  45

Leu Ala Ala Ala Asp Val Ala Val Gly Leu Phe Ala Ile Pro Phe Ala
         50                  55                  60

Ile Thr Ile Ser Leu Gly Phe Cys Thr Asp Phe Tyr Gly Cys Leu Phe
 65                  70                  75                  80

Leu Ala Cys Phe Val Leu Val Leu Thr Gln Ser Ser Ile Phe Ser Leu
                 85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
        115                 120                 125

Leu Trp Val Leu Ala Phe Gly Ile Gly Leu Thr Pro Phe Leu Gly Trp
    130                 135                 140

Asn Ser Lys Asp Ser Ala Thr Asn Asn Cys Thr Glu Pro Trp Asp Gly
145                 150                 155                 160
```

```
Thr Thr Asn Glu Ser Cys Cys Leu Val Lys Cys Leu Phe Glu Asn Val
                165                 170                 175

Val Pro Met Ser Tyr Met Val Tyr Phe Asn Phe Gly Cys Val Leu
            180                 185                 190

Pro Pro Leu Leu Ile Met Leu Val Ile Tyr Ile Lys Ile Phe Leu Val
                195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
                260                 265                 270

Asn Met Ala Ile Leu Leu Ser His Ala Asn Ser Val Val Asn Pro Ile
                275                 280                 285

Val Tyr Ala Tyr Arg Asn Arg Asp Phe Arg Tyr Thr Phe His Lys Ile
            290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330

<210> SEQ ID NO 17
<211> LENGTH: 957
<212> TYPE: DNA
<213> ORGANISM: Homo sapiens

<400> SEQUENCE: 17
atgcccaaca acagcactgc tctgtcattg gccaatgtta cctacatcac catggaaatt      60
ttcattggac tctgcgccat agtgggcaac gtgctggtca tctgcgtggt caagctgaac     120
cccagcctgc agaccaccac cttctatttc attgtctctc tagccctggc tgacattgct     180
gttggggtgc tggtcatgcc tttggccatt gttgtcagcc tgggcatcac aatccacttc     240
tacagctgcc ttttatgac ttgcctactg cttatcttta cccacgcctc catcatgtcc      300
ttgctggcca tcgctgtgga ccgatacttg cgggtcaagc ttaccgtcag atacaagagg     360
gtcaccactc acagaagaat atggctggcc ctgggccttt gctggctggt gtcattcctg     420
gtgggattga cccccatgtt tggctggaac atgaaactga cctcagagta ccacagaaat     480
gtcaccttcc tttcatgcca atttgtttcc gtcatgagaa tggactacat ggtatacttc     540
agcttcctca cctggatttt catccccctg gttgtcatgt cgccatcta tcttgacatc      600 ttttacatca ttcggaacaa actcagtctg aacttatcta actccaaaga gacaggtgca     660
ttttatggac gggagttcaa gacggctaag tccttgtttc tggttctttt cttgtttgct     720
ctgtcatggc tgcctttatc tatcatcaac tgcatcatct actttaatgg tgaggtacca     780
cagcttgtgc tgtacatggg catcctgctg tcccatgcca actccatgat gaaccctatc     840
gtctatgcct ataaaataaa gaagttcaag gaaacctacc ttttgatcct caaagcctgt     900
gtggtctgcc atccctctga ttctttggac acaagcattg agaagaattc tgagtag       957

<210> SEQ ID NO 18
<211> LENGTH: 318
<212> TYPE: PRT
<213> ORGANISM: Homo sapiens
```

<400> SEQUENCE: 18

```
Met Pro Asn Asn Ser Thr Ala Leu Ser Leu Ala Asn Val Thr Tyr Ile
1               5                   10                  15
Thr Met Glu Ile Phe Ile Gly Leu Cys Ala Ile Val Gly Asn Val Leu
            20                  25                  30
Val Ile Cys Val Val Lys Leu Asn Pro Ser Leu Gln Thr Thr Thr Phe
        35                  40                  45
Tyr Phe Ile Val Ser Leu Ala Leu Ala Asp Ile Ala Val Gly Val Leu
    50                  55                  60
Val Met Pro Leu Ala Ile Val Val Ser Leu Gly Ile Thr Ile His Phe
65                  70                  75                  80
Tyr Ser Cys Leu Phe Met Thr Cys Leu Leu Leu Ile Phe Thr His Ala
                85                  90                  95
Ser Ile Met Ser Leu Leu Ala Ile Ala Val Asp Arg Tyr Leu Arg Val
            100                 105                 110
Lys Leu Thr Val Arg Tyr Lys Arg Val Thr Thr His Arg Arg Ile Trp
        115                 120                 125
Leu Ala Leu Gly Leu Cys Trp Leu Val Ser Phe Leu Val Gly Leu Thr
    130                 135                 140
Pro Met Phe Gly Trp Asn Met Lys Leu Thr Ser Glu Tyr His Arg Asn
145                 150                 155                 160
Val Thr Phe Leu Ser Cys Gln Phe Val Ser Val Met Arg Met Asp Tyr
                165                 170                 175
Met Val Tyr Phe Ser Phe Leu Thr Trp Ile Phe Ile Pro Leu Val Val
            180                 185                 190
Met Cys Ala Ile Tyr Leu Asp Ile Phe Tyr Ile Ile Arg Asn Lys Leu
        195                 200                 205
Ser Leu Asn Leu Ser Asn Ser Lys Glu Thr Gly Ala Phe Tyr Gly Arg
    210                 215                 220
Glu Phe Lys Thr Ala Lys Ser Leu Phe Leu Val Leu Phe Leu Phe Ala
225                 230                 235                 240
Leu Ser Trp Leu Pro Leu Ser Ile Ile Asn Cys Ile Ile Tyr Phe Asn
                245                 250                 255
Gly Glu Val Pro Gln Leu Val Leu Tyr Met Gly Ile Leu Leu Ser His
            260                 265                 270
Ala Asn Ser Met Met Asn Pro Ile Val Tyr Ala Tyr Lys Ile Lys Lys
        275                 280                 285
Phe Lys Glu Thr Tyr Leu Leu Ile Leu Lys Ala Cys Val Val Cys His
    290                 295                 300
Pro Ser Asp Ser Leu Asp Thr Ser Ile Glu Lys Asn Ser Glu
305                 310                 315
```

<210> SEQ ID NO 19
<211> LENGTH: 1739
<212> TYPE: DNA
<213> ORGANISM: Homo sapiens

<400> SEQUENCE: 19

```
cgtcctacag cattctggaa acttgaggat gtgcggtgca taaggggct ggaagtgacc    60
cacctgtgat gagcccttc taaggagaag ggtttccaag agatcacccc accagaaaag   120
ggtaggaatg agcaagttgg gaattttaga ctgtcactgc acatggacct ctgggaagac   180
gtctggcgag agctaggccc actggcccta cagacggatc ttgctggctc acctgtccct   240
gtggaggttc ccctgggaag gcaagatgcc caacaacagc actgctctgt cattggccaa   300
```

```
tgttacctac atcaccatgg aaattttcat tggactctgc gccatagtgg gcaacgtgct      360
ggtcatctgc gtggtcaagc tgaaccccag cctgcagacc accaccttct atttcattgt      420
ctctctagcc ctggctgaca ttgctgttgg ggtgctggtc atgcctttgg ccattgttgt      480
cagcctgggc atcacaatcc acttctacag ctgcctttt atgacttgcc tactgcttat       540
ctttacccac gcctccatca tgtccttgct ggccatcgct gtggaccgat acttgcgggt      600
caagcttacc gtcagataca agagggtcac cactcacaga gaatatggc tggccctggg       660 cctttgctgg ctggtgtcat tcctggtggg attgaccccc atgtttggct ggaacatgaa      720
actgacctca gagtaccaca gaaatgtcac cttcctttca tgccaatttg tttccgtcat      780
gagaatggac tacatggtat acttcagctt cctcacctgg atttcatcc cctggttgt        840 catgtgcgcc atctatcttg acatctttta catcattcgg aacaaactca gtctgaactt      900
atctaactcc aaagagacag gtgcatttta tggacgggag ttcaagacgg ctaagtcctt      960
gtttctggtt ctttctcttgt tgctctgtc atggctgcct ttatctatca tcaactgcat     1020
catctacttt aatggtgagg taccacagct tgtgctgtac atgggcatcc tgctgtccca     1080
tgccaactcc atgatgaacc ctatcgtcta tgcctataaa ataaagaagt tcaaggaaac     1140
ctaccttttg atcctcaaag cctgtgtggt ctgccatccc tctgattctt tggacacaag     1200
cattgagaag aattctgagt agttatccat cagagatgac tctgtctcat tgaccttcag     1260
attccccatc aacaaacact tgagggcctg tatgcctggg ccaagggatt tttacatcct     1320
tgattacttc cactgaggtg ggagcatctc cagtgctccc caattatatc tcccccactc     1380
cactactctc ttcctccact tcattttcc tttgtccttt ctctctaatt cagtgtttg       1440 gaggcctgac ttggggacaa cgtattattg atattattgt ctgttttcct tcttcccaat     1500
agaagaataa gtcatggagc ctgaaggggtg cctagttgac ttactgacaa aaggctctag    1560
ttgggctgaa catgtgtgtg gtggtgactc atttccatgc cattgtggaa ttgagcagag     1620
aacctgctct cggaggatgc ctagaagatg ttgggaacag aagaaataaa ctgagtttaa     1680 ggggactta aactgctgaa ttcacctgtg gatgttttg agtaaataaa agctaatag        1739
```

<210> SEQ ID NO 20
<211> LENGTH: 318
<212> TYPE: PRT
<213> ORGANISM: Homo sapiens

<400> SEQUENCE: 20

Met Pro Asn Asn Ser Thr Ala Leu Ser Leu Ala Asn Val Thr Tyr Ile
1               5                   10                  15

Thr Met Glu Ile Phe Ile Gly Leu Cys Ala Ile Val Gly Asn Val Leu
            20                  25                  30

Val Ile Cys Val Val Lys Leu Asn Pro Ser Leu Gln Thr Thr Thr Phe
        35                  40                  45

Tyr Phe Ile Val Ser Leu Ala Leu Ala Asp Ile Ala Val Gly Val Leu
    50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
                85                  90                  95

Ser Ile Met Ser Leu Leu Ala Ile Ala Val Asp Arg Tyr Leu Arg Val
            100                 105                 110

Lys Leu Thr Val Arg Tyr Lys Arg Val Thr Thr His Arg Arg Ile Trp

```
            115                 120                 125
Leu Ala Leu Gly Leu Cys Trp Leu Val Ser Phe Leu Val Gly Leu Thr
    130                 135                 140
Pro Met Phe Gly Trp Asn Met Lys Leu Thr Ser Glu Tyr His Arg Asn
145                 150                 155                 160
Val Thr Phe Leu Ser Cys Gln Phe Val Ser Val Met Arg Met Asp Tyr
                165                 170                 175
Met Val Tyr Phe Ser Phe Leu Thr Trp Ile Phe Ile Pro Leu Val Val
                180                 185                 190
Met Cys Ala Ile Tyr Leu Asp Ile Phe Tyr Ile Arg Asn Lys Leu
                195                 200                 205
Ser Leu Asn Leu Ser Asn Ser Lys Glu Thr Gly Ala Phe Tyr Gly Arg
    210                 215                 220
Glu Phe Lys Thr Ala Lys Ser Leu Phe Leu Val Leu Phe Leu Phe Ala
225                 230                 235                 240
Leu Ser Trp Leu Pro Leu Ser Ile Ile Asn Cys Ile Ile Tyr Phe Asn
                245                 250                 255
Gly Glu Val Pro Gln Leu Val Leu Tyr Met Gly Ile Leu Leu Ser His
                260                 265                 270
Ala Asn Ser Met Met Asn Pro Ile Val Tyr Ala Tyr Lys Ile Lys Lys
                275                 280                 285
Phe Lys Glu Thr Tyr Leu Leu Ile Leu Lys Ala Cys Val Val Cys His
    290                 295                 300
Pro Ser Asp Ser Leu Asp Thr Ser Ile Glu Lys Asn Ser Glu
305                 310                 315

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
ggaggacctt acctgttcgt ga                                         22

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gaacaacaca ctccatgcgg                                            20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
atgtgcttcc cttatcaaac ct                                         22

<210> SEQ ID NO 24
<211> LENGTH: 21
<212> TYPE: DNA
<213> ORGANISM: Artificial Sequence
```

```
-continued

<220> FEATURE:
<223> OTHER INFORMATION: primer

<400> SEQUENCE: 24
cttgtgcttg gacgagaact g                                                   21
```